United States Patent [19]

Georgi

[11] 4,313,445
[45] Feb. 2, 1982

[54] ELECTRONIC SPHYGMOMANOMETER

[75] Inventor: Heinz W. Georgi, Del Mar, Calif.

[73] Assignee: IVAC Corporation, San Diego, Calif.

[21] Appl. No.: 845,081

[22] Filed: Oct. 25, 1977

[51] Int. Cl.³ .............................................. A61B 5/02
[52] U.S. Cl. .................................. 128/680; 128/682;
364/417
[58] Field of Search .............................. 128/677–686,
128/415–417

[56] References Cited
U.S. PATENT DOCUMENTS

| | | | |
|---|---|---|---|
| 3,450,131 | 6/1969 | Vogt | 128/682 |
| 3,533,401 | 10/1970 | Streu | 128/682 |
| 3,552,383 | 1/1971 | Krueger et al. | 128/683 |
| 3,633,568 | 1/1972 | Hobel | 128/682 |
| 3,814,083 | 6/1974 | Fletcher et al. | 128/683 |
| 3,885,551 | 5/1975 | Massie | 128/682 |
| 3,939,824 | 2/1976 | Arneson et al. | 128/672 |
| 4,026,277 | 5/1977 | Toda et al. | 128/680 |
| 4,058,117 | 11/1977 | Kaspari et al. | 128/682 |
| 4,105,020 | 8/1978 | Matsuoka et al. | 128/682 |
| 4,144,879 | 3/1979 | Nakayama et al. | 128/680 |

OTHER PUBLICATIONS

Schulze, A. E. et al., "A System for Aut. Meas. and Dig. Display of S/D Blood Pressures", SW IEEE Conf. Rec., Apr. 1968, pp. 17F1–17F5.
Watanabe, S. et al., "New Electr. Sphyg. lets Patients Monitor BP Unassisted", JEE No. 107, pp. 12–16, Oct. 1975.
Graham, M., "UPs Monitor EKG and BP", Electronics Design 19, Sep. 13, 1976, p. 28.

Primary Examiner—Robert W. Michell
Assistant Examiner—Francis J. Jaworski
Attorney, Agent, or Firm—Fulwider, Patton, Rieber, Lee & Utecht

[57] ABSTRACT

An electronic method and apparatus for automatically determining systolic and diastolic blood pressure and heart rate by accurately detecting, verifying and evaluating the full stream of korotkoff sounds produced as electrical signals from a microphone in a cuff occluding the brachial artery of a patient. Waveform analysis is first performed upon the incoming signal waveforms by an analog prescreening subsystem to initially separate true korotkoff sound signals from a variety of artifact and noise signals and to provide an output pulse stream correctly indicating korotkoff sound occurrences in the time and blood pressure domain, with each pulse proportional in amplitude to the amplitude of the corresponding korotkoff sound represented. The output korotkoff sound pulse stream is then digitized by an analog to digital converter and further analyzed by a digital processing subsystem to additionally remove any noise and artifact signals passed as otherwise misleading quasi-korotkoff sound pulses by the prescreening subsystem, to modify and certify the resultant data as either reliable or suspect, to determine heart rate and the most probable values for systolic and diastolic blood pressure levels indicated by the signal stream detected during the measurement cycle.

99 Claims, 40 Drawing Figures

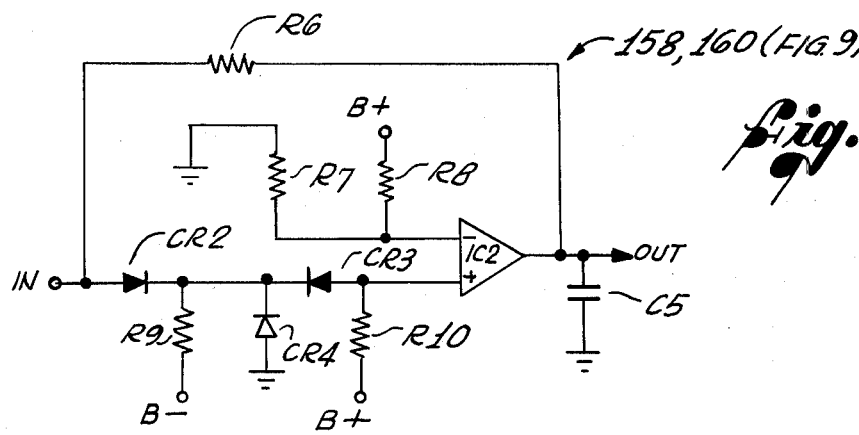
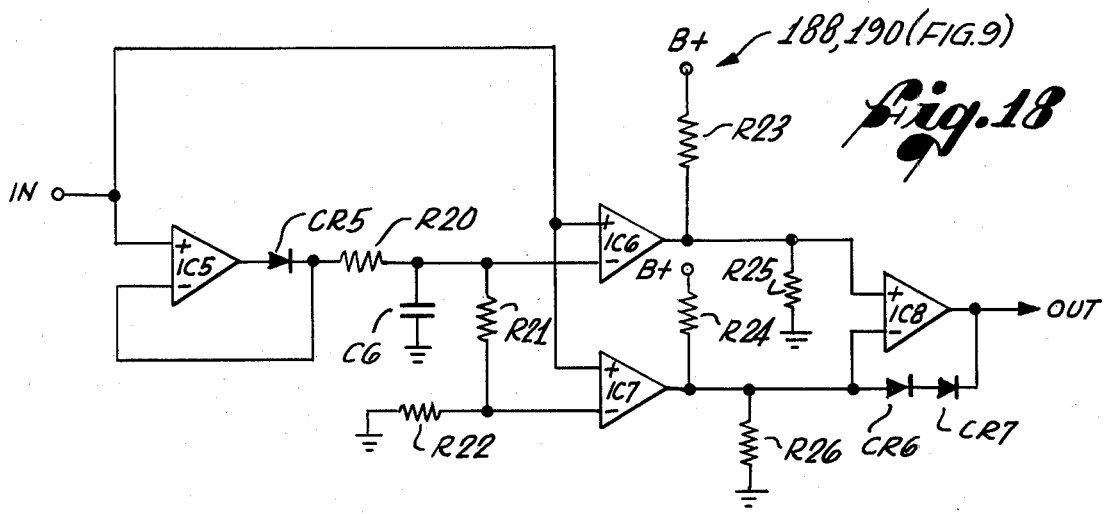
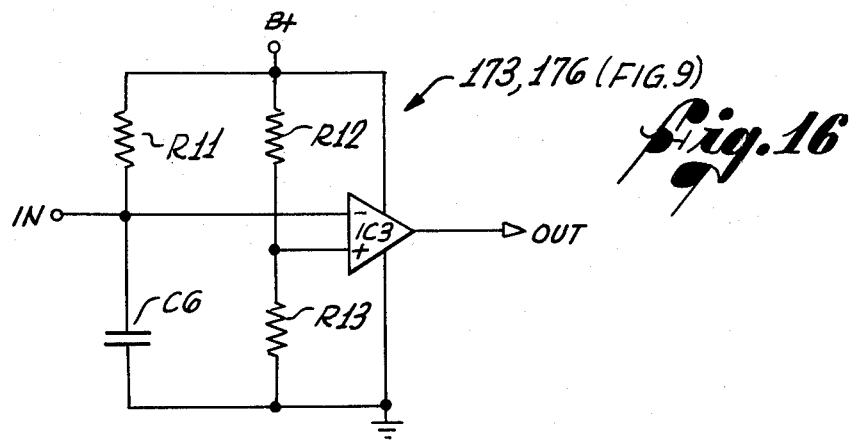

4,313,445

ELECTRONIC SPHYGMOMANOMETER

BACKGROUND OF THE INVENTION

This invention relates generally to improvements in methods and apparatus for the measurement of blood pressure and heart rate and, more particularly, to a new and improved electronic sphygmomanometer system enabling very rapid, accurate, reliable and easily obtained blood pressure and heart rate measurements.

It is common practice in the medical arts, as in hospitals and doctors' offices, to employ an auscultation technique for measuring the blood pressure of a patient by using the characteristics of the so-called korotkoff sounds to determine the systolic and diastolic values of the patient's blood pressure.

The korotkoff method typically makes use of an inflatable cuff surrounding a portion of the patient's upper arm. Sufficient inflation of the cuff closes off or completely occludes the brachial artery of the patient. As air is released and the cuff is slowly deflated, a point is reached at which the occluded artery begins to open for a very brief period during each cardiac cycle. At this point, the cuff pressure, which is assumed in using this process as being approximately equal to the blood pressure in the brachial artery, will be that of the peak pressure obtained during the cardiac cycle, this pressure being known in the medical arts as the systolic blood pressure.

Detection of the point at which the artery first opens may be made by any suitable listening device such as a stethoscope or microphone applied to the arm over the artery, usually downstream of the inflated cuff. As the artery opens, auscultatory sounds caused by the pulsating blood flow or turbulence in the blood stream below the occlusion are sensed by the listening device, and these sounds are referred to in the medical arts as the well known korotkoff sounds. At the point of first detection, where the decreasing cuff pressure is matched by the maximum blood pressure, medical personnel skilled in the auscultation technique can detect the pulsatile blood flow in the artery and the onset of korotkoff sounds, and thereby determine the systolic blood pressure.

As the pressure in the cuff continues to drop, the korotkoff sounds continue substantially in synchronization with the blood pressure pulses produced during successive cardiac cycles. Eventually a point is reached at which the artery remains open during the entire cardiac cycle and, at this point, the korotkoff sounds cease entirely. The cuff pressure at this point approximates the lowest blood pressure reached during the cardiac cycle, with the heart essentially at rest, and this is known as the diastolic blood pressure.

Hence, it will be apparent that, if values of the decreasing cuff pressure are correlated with the korotkoff sound output of the stethoscope or microphone, the cuff pressure at the time the first korotkoff sound occurs is approximately equal to the systolic blood pressure, while the cuff pressure at the time the last korotkoff sound occurs is approximately equal to the diastolic blood pressure encountered during the measurement process.

It will be apparent from the foregoing that conventional blood pressure measurement procedures using an inflatable cuff and a suitable listening device are prone to a number of significant deficiencies. In this regard, medical personnel making such measurements are required to make rather difficult determinations regarding the presence or absence of korotkoff sounds which may be of relatively low and difficult to detect amplitudes and are often intermixed and easily confused with ambiguous signals generated by artifacts and both internal and external noise. In this regard, noise and artifact signals generally appear to be produced more frequently in sick patients than in healthy patients so that the process is oftentimes more difficult to perform accurately in those instances where the very requirement for a high degree of accuracy is greatest. In addition, the determination of the end points for the onset and cessation of the korotkoff sound pulse train is somewhat subjective and therefore subject to further inaccuracy in the absence of considerable training and much experience on the part of skilled medical personnel.

Since there are relatively few persons really capable of taking accurate blood pressure measurements using conventional manual auscultation techniques, various attempts have been made in the prior art to eliminate the aforedescribed deficiencies by mechanizing the measurement process so that the subjective factors introduced when an untrained person attempts to measure blood pressures can be eliminated and, further, to provide some discrimination against artifacts and noise. However, such automatic systems for measuring blood pressure and, typically, associated heart rate, have generally proven to be overly sensitive to spurious signals generated by artifacts and noise and have proven, therefore, to be in many instances less accurate than medical personnel using tried and true manual procedures. As a consequence, automatic korotkoff sound monitoring systems for determining blood pressure have experienced only limited acceptance by the medical profession.

Hence, those concerned with the development and use of automatic sphygmomanometers in the medical field have long recognized the need for improved sphygmomanometer systems which enable more accurate and reliable blood pressure and heart rate measurements to be made and which obviate the need for a high degree of skill and subjective expertise on the part of medical personnel making such measurements. The present invention fulfills all of these needs.

SUMMARY OF THE INVENTION

Briefly, and in general terms, the present invention provides a new and improved sphygmomanometer system embodying novel methods and apparatus for accurately and reliably detecting, filtering, analyzing, verifying and evaluating a korotkoff sound signal stream in determining systolic and diastolic blood pressures and heart rate for a patient being monitored during a measurement cycle.

Basically, the present invention is directed to an improved electronic method and apparatus for verifying and certifying the genuineness of korotkoff sound signals with a high degree of reliability and separating such true korotkoff sound signals from a variety of artifact and noise signals intermixed with the korotkoff sound signals in the incoming data stream. This is accomplished by waveform analysis first performed upon all of the incoming signal waveforms by means of an analog prescreening subsystem. The analog analysis and filtering process is then continued and further enhanced in a digital processing subsystem imposing additional analysis constraints upon the data to further eliminate any contributions due to noise and artifact signals remaining in the data stream as potentially misleading quasi-korotkoff sound signals and to determine heart rate. The digital processing subsystem then modifies and certifies the resultant data as either reliable or unreliable and applies a plurality of novel manipulations and tests upon the resultant data to determine the most probable values for systolic and diastolic blood pressure levels as indicated by the incoming signal stream detected during the measurement cycle performed upon the patient.

In accordance with the invention, the auscultatory korotkoff sounds are detected by a microphone and the electrical signal output from the microphone is analyzed in a three channel analog prescreening subsystem which filters the incoming data and provides as electrical output a pulse train correctly correlating and marking the locations of korotkoff sound signals in the time and blood pressure domains, with each output pulse being proportional in amplitude to the amplitude of the corresponding korotkoff sound signal represented. The analog prescreening subsystem performs waveform analysis upon all of the incoming signal waveforms, based upon the discovery of certain unique characteristics associated with those waveforms correctly depicting true korotkoff sound signals, in contrast with those waveforms representing a variety of artifact and noise signals. In this connection, it has been discovered that waveform characteristics of the incoming signals, as opposed to frequency characteristics, provide the most reliable means for accurately separating korotkoff sound signals from an electrical signal environment which also includes artifact and noise signals falling within the typical frequency domain associated with true korotkoff sound signals.

It has been discovered, in the development of the present invention, that true korotkoff sound signals produced as incoming data from a microphone transducer always assume one of two general classes of waveform configurations, or hybrid waveforms in between these two classes of waveform configurations which still possess certain key characteristics of one or both general classes, all of which are subject to prescribed analysis and recognition by the system of the present invention. These characteristics include waveform shape, size and direction as measured by polarity, amplitude, slope and timing.

In this regard, it has been determined that diastolic korotkoff sound signals, i.e., those signal waveforms in the korotkoff sound signal stream closer to the lower, diastolic blood pressure end of the korotkoff signal spectrum, always have a precursor in the form of a slowly rising, relatively low frequency region defining a bulge prior to the onset of the oppositely directed korotkoff spike in the waveform. The resultant slowly rising and oppositely directed precursor bulge leading the korotkoff spike will, if the signal waveform depicts a true korotkoff sound, satisfy certain constraints imposed upon the waveform by the analysis performed in the analog prescreening subsystem regarding minimum amplitude threshold, minimum time duration and minimum area under the bulge, all of which are characteristic of true korotkoff signals and essentially exclude most artifact and noise signals. While this diastolic waveform is typically associated with the diastolic region of the korotkoff sound pulse spectrum, it can also occur anywhere in the pulse spectrum, including the systolic pressure region of the pulse spectrum.

Similarly, it has been determined that there exists a second class of waveform, occurring at times at the systolic end of the korotkoff signal spectrum, characterized by a relatively slow leading edge for the korotkoff spike followed by a relatively rapid trailing edge for the spike, and this waveform is also subject to reliable analysis constraints regarding minimum time duration and minimum slope which characterize it as being indicative of a true korotkoff sound signal, again in contrast with spurious artifacts and noise signals.

In addition, it has been further discovered that, independent of polarity, the base to peak amplitude of the korotkoff pulse or spike in the incoming electrical waveform is most reliably determined on the fast, trailing edge of the spike than on the oftentimes much slower leading edge of the spike which is more frequently simulated by low frequency artifacts.

Hence, in accordance with the present invention, the analog prescreening subsystem provides three analysis channels for processing all incoming signal waveforms, a first spike channel to measure the amplitude of the korotkoff sound signal and produce an output pulse proportional to that amplitude, a so-called diastolic channel which correlates the incoming signal waveform with the aforementioned generalized diastolic waveform characteristic to indicate the occurrence of a true korotkoff sound signal, and a systolic channel which correlates all of the incoming signal waveforms with the aforementioned generalized systolic waveform characteristic to likewise certify the occurrence of a true korotkoff sound signal.

The diastolic and systolic channels provide verification outputs only upon recognition of a true korotkoff sound signal occurrence. These electrical outputs from the diastolic and systolic channels in turn gate the pulse output from the spike channel, so that the amplitude and time correlated pulses produced by the spike channel will normally be blocked from appearing as electrical output from the analog prescreening subsystem unless the spike channel gate is simultaneously opened by a verified true korotkoff signal output from either the diastolic analysis channel, the systolic analysis channel, or both. In this latter regard, signal waveforms may occur in the incoming data which possess waveform characteristics acceptable to both the systolic and diastolic analysis channels or acceptable to only one of them, but a "true" output from either analysis channel is sufficient to gate "on" the electrical pulse output from the spike channel, so that they can be passed on to the digital processing subsystem for further analysis.

In the analog prescreening subsystem, the incoming signal waveforms first undergo preamplification and frequency shaping prior to being inputted to the diastolic and systolic analysis channels, to remove extremely low frequency and high frequency artifact and noise signals and provide an acceptance region of approximately ½ Hz. to 15 or 20 Hz. in the frequency domain.

In the diastolic analysis channel, the incoming signal is first rectified to isolate the relatively slow precursor bulge on the opposite side of the time axis from the korotkoff spike and the resultant signal is then integrated above a prescribed minimum amplitude threshold in an integration system which requires a prescribed minimum time duration in order to reach saturation. The integrated area under the rectified curve is then passed through a discriminator stage to determine whether or not the area is of sufficient magnitude to justify certification from the diastolic analysis channel as a true korotkoff sound signal waveform.

In the systolic analysis channel, the incoming signal is also first rectified to isolate the slowly rising leading edge of the korotkoff spike from the waveform of opposite polarity on the opposite side of the time axis. The remaining signal is then differentiated to produce an output pulse proportional in height to the amplitude of the leading edge slope and correlated in width with the time duration of the leading edge. The resultant pulse is then tested by a discriminator stage to determine if the amplitude meets the minimum slope requirements for the leading edge, while the width of the pulse is tested by a timing stage which requires a minimum "on" time at the input to the timer before the timer will produce a "true" output. If the incoming signal waveform to the systolic analysis channel satisfies both of the tests imposed by the discriminator and timing stages, the systolic channel produces a "true" output which certifies the incoming signal waveform as being properly correlated with the occurrence of a korotkoff sound.

Both outputs, from the diastolic analysis channel and the systolic analysis channel, are passed through an OR gate to the input of a time stretcher which, upon being energized by an input signal, produces a sustained "true" output signal of fixed duration after termination of the input signal. The electrical output of the time stretcher is utilized to gate the electrical pulse output of the spike channel.

In the spike channel, the incoming signal waveform again undergoes preliminary frequency shaping to establish a frequency domain for accepted signals between approximately $\frac{1}{2}$ Hz. and 150 Hz. However, the region between $\frac{1}{2}$ Hz. and approximately 5 Hz. is attenuated relative to the region between approximately 15 Hz. and 150 Hz. so that the primary frequency range is the latter 15 Hz. to 150 Hz. range, but some low frequency signal is permitted to leak through the input to the spike channel. Hence, while low frequency noise and artifact signals are substantially attenuated, sufficient low frequency is present to position the korotkoff spike on the opposite side of the time axis from the precursor bulge often associated with the diastolic korotkoff signal waveforms and which may be of sufficiently large magnitude to otherwise bias the spike sufficiently so that it is substantially translated to the opposite side of the time axis.

The frequency shaped signal in the spike channel is thereafter first rectified to eliminate the low frequency content entirely and extract the spike which has been now shifted to the proper side of the time axis, and the rectified signal is subsequently differentiated and again rectified to isolate the trailing edge slope portion of the korotkoff spike waveform.

If a "true" output has been provided by either the diastolic analysis channel, the systolic analysis channel, or both, to the control gate in the spike channel, the pulse output representing the differentiated trailing edge of the korotkoff spike is passed to an integrator. The integrator essentially reverses the differentiation process in the spike channel and produces as its output a pulse having an amplitude proportional in height to the amplitude of the spike portion of the korotkoff sound signal waveform, from its peak to its base at the time axis, but limited to measurement along the trailing edge of the korotkoff spike. This is the final output from the analog prescreening subsystem, and indicates the magnitude and occurrence of true korotkoff sound signals in the time and blood pressure domains as produced by three channel waveform analysis performed upon all of the incoming signal waveforms to the sphygmomanometer system.

An additional electrical subsystem is provided, in accordance with the present invention, to prevent distortion of the amplitude of the output pulses from the analog prescreening subsystem by preventing the piling up of additional low amplitude pulse contributions, due to pulse ringing. Such a condition might be produced by continued integration in the output integrator stage of the lesser pulses to provide a misleading single high amplitude pulse output or a series of secondary pulses. In this connection, a peak rectifier and discriminator latch also receive the differentiated and rectified output from the spike channel prior to integration and provide a variable integration threshold for the output integrator stage which effectively prevents the integrator from accepting and integrating smaller pulses for a period of time after a larger genuine korotkoff spike pulse has been accepted.

The output korotkoff sound pulse stream from the analog prescreening subsystem is then digitized by an analog to digital converter and further analyzed by the digital processing subsystem to additionally remove any noise and artifact signals passed as otherwise misleading quasi-korotkoff sound pulses, to modify and certify the resultant data as either reliable or suspect, to determine heart rate and the most probable values for systolic and diastolic blood pressure levels.

The digital processing subsystem, in accordance with the invention, not only performs further analysis upon the korotkoff sound pulse stream from the analog prescreening subsystem, but also performs other control functions relating to start-up of the system and conditioning of the system to enable the measurement process to proceed. This includes control of the inflation of the cuff upon the arm of the patient, the determination that the inflation has reached a proper level to enable proper data to be obtained, prevention of over-inflation, and initiation and control of deflation, as well as dumping of the remaining pressure in the cuff after sufficient information has been obtained to make all of the required blood pressure and heart rate determinations. The latter dumping of cuff pressure minimizes extended occlusion of the patient's artery beyond the time needed to complete the measurement process.

The first data manipulation performed in the digital processing subsystem in accordance with the present invention is the selection of the most reliable range in the korotkoff sound pulse stream, to determine what is referred to as the "mid-range". This is essentially accomplished by averaging the pulse amplitudes in groups to locate the peak amplitude and mark the locations of the half-peak amplitudes on both sides of the maximum peak, the mid-range region extending between the two half amplitude locations.

At this point the korotkoff pulse data remains unchanged and is still stored in a shift register memory as it was received from the prescreening subsystem, the mid-range determination having no effect upon the data except the establishment of the most reliable range for further computation and examination.

The next procedure performed by the digital processing subsystem of the present invention involves the determination of the average amplitude of the korotkoff sound pulses within the previously determined mid-range region. Initially, all korotkoff sound signals in the mid-range are added and the average computed. This averaging process is then repeated after first ignoring all amplitudes smaller than one-half of the average amplitude determined in the first averaging process, and a new average is thereby computed which serves to eliminate the contribution to the averaging process of low amplitude noise spikes and artifacts. If the computed average is less than a predetermined minimum, further analysis is abandoned and the measurement process is terminated, with an indication being provided to the operator that the signal data is too low in amplitude to be reliable.

The next procedure performed by the digital processing subsystem involves the determination of the average pulse period in the mid-range region. Again, the average period is first determined between the highest and lowest korotkoff sound pulses, i.e., between the half peak amplitude korotkoff pulses defining the mid-range region. This average is then recomputed after first ignoring the contribution of those pulse periods less than one-half of the previously determined average pulse period, to again eliminate any contribution to the averaging process by noise and artifact signals, and provide a reliable final average pulse period. If the resultant average pulse period is too long, indicating a heart rate below a prescribed minimum rate, the analysis process is again aborted, and a "low signal" indication is displayed to the operator, whereas an unusually short pulse period indicating an excessively high heart rate will likewise terminate the analysis process and indicate that too many artifacts in the data are being accepted by the system as true korotkoff sound signals, thereby calling for a repeat of the measurement process.

Up to this point, all korotkoff sound signals had been stored in the shift register memory unchanged from the original storage provided at the output of the analog prescreening subsystem. Subsequently, the digital processing subsystem of the present invention modifies the stored data by normalizing all of the korotkoff pulses to a standardized average and then performing various spreading and smoothing techniques to ultimately provide a smoothed, digitized waveform envelope for the korotkoff sound pulse stream upon which systolic and diastolic blood pressure measurements can be reliably made.

In accordance with the invention, a variety of tests are performed at the extremities of the smoothed, digitized waveform, including location of minimum amplitude or slope reversal limits, pulse period tests, and systolic and diastolic slope projections, to determine three categories of diastolic pressure limits and two categories of systolic pressure limits which are subsequently used in the final determinations of the most probable and reliable systolic and diastolic blood pressure levels of the patient.

The new and improved electronic sphygmomanometer system of the present invention is extremely accurate, reliable and easy to use. The system provides enhanced precision in screening true korotkoff sound signals from artifact and noise signals and is quick to inform medical personnel of any conditions which indicate the presence of unreliable data. Hence, the system of the present invention minimizes the time consuming and error-prone aspects of manual techniques for measurements of human blood pressure and heart rate and obviates the need for a high degree of skill and subjective expertise on the part of medical personnel required to make such measurements.

These and other objects and advantages of the invention will become apparent from the following more detailed description, when taken in conjunction with the accompanying drawings of illustrative embodiments.

DESCRIPTION OF THE DRAWINGS

FIG. 15 is an electrical schematic diagram of one embodiment of a rectifier-integrator combination suitable for use in the analog prescreening subsystem of the invention;

FIG. 16 is an electrical schematic diagram of one embodiment of timing circuitry suitable for use in the analog prescreening subsystem of the present invention;

extended to the frequency limits previously indicated without departing from the invention.

Figure 13:
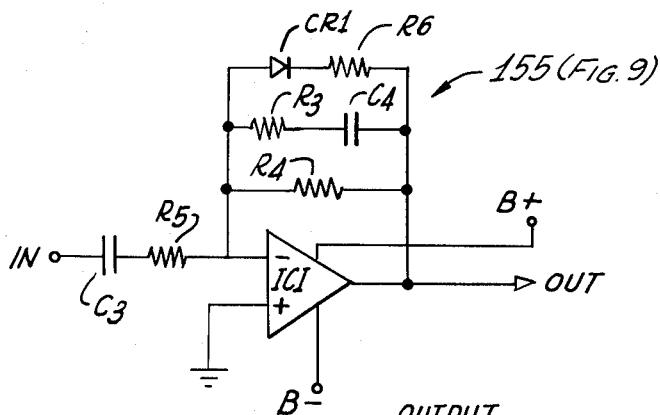
FIG. 13 is an electrical schematic diagram of a frequency shaping amplifier used in the analog prescreening subsystem of the invention.

One example of an electrical circuit suitable for carrying out the frequency shaping and inverting functions of the amplifier 155 is shown in FIG. 13, wherein:
- R6=27 kilohms
- R3=10 kilohms
- R4=68 kilohms
- R5=10 kilohms
- C3=33 microfarads
- C4=0.1 microfarads
- CR1=Type 1N4148
- B+=+5 volts
- B−=−10 volts
- IC1=LM324 manufactured by National Semiconductor Corp., 2900 Semiconductor Drive, Santa Clara, Calif.

Figure 14:
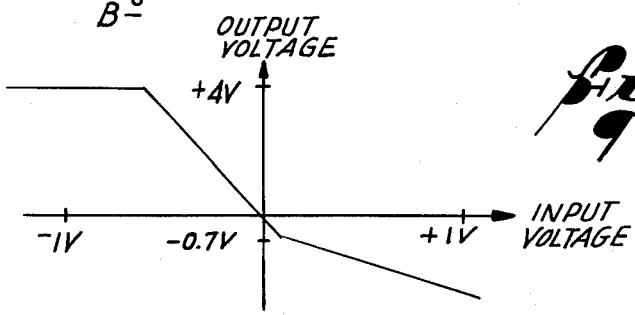
FIG. 14 illustrates the electrical gain characteristic of the amplifier shown in FIG. 13.

FIG. 14 illustrates the electrical gain characteristic of the frequency shaping amplifier 155 shown in FIG. 13. The gain factor is 6.8 from 0.5 Hz. to 23 Hz., and the electrical output saturates at positive outputs greater than 4 volts. The gain is reduced to a factor of approximately 2 for negative voltages exceeding −0.7 volts. These values are not to be considered as limiting, but merely as illustrative of a presently preferred embodiment for practicing the present invention.

The electrical output of the amplifier 155 is passed as input over line 156 to the diastolic waveform analysis channel where the incoming signal is first rectified by a rectifier 158 to isolate the relatively slow precursor bulge on the positive side of the time axis from the negative going korotkoff spike. The rectified signal is then directed as output over line 159 to an integrator 160 which operates in conjunction with the saturating amplifier 155, previously described, to impose several tests upon the diastolic channel input waveform. In this regard, the integrator 160 has a minimum threshold below which it will not integrate the incoming waveform, as indicated schematically by the cross-hatched area of the waveform shown as input over line 156. Hence, the integrator 160 performs initial amplitude discrimination of the diastolic waveform. Above the minimum threshold, the integrator 160 essentially integrates at a rate proportional to the actual amplitude of the precursor bulge. An additional upper limit for the precursor bulge (not shown on the diastolic waveform adjacent line 156) is imposed by the saturation characteristics of the amplifier 155, as previously indicated by the gain characteristic shown in FIG. 14.

Figure 12:
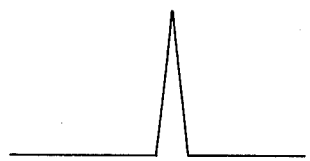
FIG. 12 illustrates a generalized representation of a high amplitude, short duration artifact or noise pulse which may be encountered by the system of the present invention in the monitored data signal stream.

The cooperation between the amplifier 155 and the integrator 160 is such that it imposes the requirement for a prescribed minimum time duration of the precursor bulge in order for the integrator 160 to reach saturation. The reason for having such an arrangement is to prevent a large amplitude, short duration noise or artifact spike, such as that shown, for example, in FIG. 12 of the drawings, from providing an acceptable area integration magnitude as output from the integrator 160, and thereby avoid a false korotkoff sound indication. In this regard, the high amplitude, short duration pulse in FIG. 12 may be of sufficient amplitude to meet the area requirements for certification as a true korotkoff sound. However, the time duration requirement imposed by the diastolic channel prevents the integrator from reaching a sufficient level during the integration process to identify the false waveform as a true korotkoff sound.

One example of electrical circuitry suitable for performing the functions of the rectifier 158 and integrator 160 of the diastolic channel is shown in FIG. 15, wherein:
- R6=47 kilohms
- R7=2.61 kilohms
- R8=10 kilohms
- R9=47 kilohms
- R10=27 kilohms
- C5=1.0 microfarads
- CR2=CR3=CR4=Type IN4148
- B+=+5 volts
- B−=−10 volts
- IC2=LM339 manufactured by Semiconductor Corp.

The electrical output from the integrator 160, proportional to the area of the precursor bulge in the diastolic channel, is directed over line 161 as input to a discriminator 162 to determine whether or not the area is of sufficient magnitude to justify certification from the diastolic analysis channel as a true korotkoff sound signal waveform. If the amplitude discrimination is favorable, a "true" output is directed over line 163 as one input to an OR gate 165.

In the systolic channel, the electrical input received over line 157 is also first rectified to isolate the negative going leading edge of the korotkoff spike in the systolic waveform from that portion of the waveform of opposite polarity. The rectified signal is then passed over line 168 as input to a differentiator 169.

The differentiator 169 provides a negative electrical output signal over line 170 which is proportional in amplitude to the magnitude of the negative slope of the leading edge of the systolic waveform, the width of the output signal being correlated with the time duration of the negative going leading edge.

The signal output from the differentiator 169 is then examined by a discriminator 171 to determine if the amplitude of the negative signal meets the minimum slope requirements for the leading edge of the systolic waveform. If the amplitude requirements of the discriminator 171 are satisfied, an output is directed over line 172 as input to a timer 173 which is characterized by requiring a minimum "on" time at the input to the timer before the timer will produce a "true" output over line 174, the latter electrical output being terminated as soon as the electrical input to the timer 173 over line 172 is terminated. Hence, timer 173 tests the width of the differentiated leading edge pulse to determine whether or not it satisfies the requirements for minimum "on" time duration.

If the incoming signal waveform to the systolic analysis channel satisfies both of the tests imposed by the discriminator 171 and the timer 173, the systolic channel produces a "true" output which certifies the incoming signal waveform as being properly correlated with the occurrence of a korotkoff sound, and this "true" output is directed as a second input over line 174 to the OR gate 165.

One example of electrical circuitry suitable for performing the functions of the timer 173 is shown in FIG. 16, wherein:
- R11=15 kilohms
- R12=4.7 kilohms
- R13=4.7 kilohms
- C6=1.0 microfarads
- B+=+5 volts
- IC3=LM339 manufactured by National Semiconductor Corp.

Both of the outputs from the diastolic analysis channel and the systolic analysis channel, over lines 163 and 174, respectively, are passed through the OR gate 165 and provide a "true" output over line 175 as input to a timer stretcher stage 176. The timer stretcher 176 is characterized as producing a sustained "true" output signal for a fixed time period after termination of an energizing input signal over line 175. Electrical output of the timer stretcher 176 is directed as one enabling input over line 177 to an AND gate 178. A "true" electrical output from the AND gate 178, over line 192, provides enabling input to a control gate 186 in the korotkoff spike amplitude analysis channel, so that the korotkoff verification outputs from the diastolic and systolic channels ultimately are utilized to gate the electrical pulse output from the spike channel.

One example of electrical circuitry suitable for performing the functions of the timer stretcher 176 is also shown in FIG. 16, wherein:

$R11 = 39$ kilohms
$R12 = 10$ kilohms
$R13 = 1.0$ kilohms
$C6 = 1.0$ microfarads
$B+ = +5$ volts
$IC3 = LM339$ manufactured by National Semiconductor Corp.

The frequency shaped signal in the spike amplitude analysis channel is directed from the frequency shaping network 154 as input over line 179 to a rectifier 180, to completely extract the korotkoff spike from the slower moving, low frequency signal content, the spike having been shifted to the proper side of the time axis so that it is isolated by the rectification process.

The rectified signal is directed over line 181 as input to a differentiator 182 which produces an output waveform over line 183 wherein the negative going leading edge of the korotkoff spike and the positive going trailing edge of the korotkoff spike (referred back to the input waveform on line 151) are now on opposite sides of the time axis, with the leading edge being shown as negative and the trailing edge being shown as positive. Hence, the differentiated leading and trailing edges are fed as input to the rectifier 184 which effectively isolates the trailing edge slope portion of the korotkoff spike waveform and provides this as electrical output over line 185 to the control gate 186 for the spike analysis channel.

If a "true" output has been provided by either the diastolic analysis channel, the systolic analysis channel, or both, to the control gate 186 via the AND gate 178, the pulse output representing the differentiated trailing edge of the korotkoff spike is passed through the control gate 186 over line 194 to an integrator 195.

The integrator 195 essentially reverses the differentiation process in the spike channel and produces as its output a pulse having an amplitude proportional in height to the amplitude of the spike portion of the korotkoff sound signal waveform, measured from its peak to its base at the time axis, but limited to measurement along the positive going trailing edge of the korotkoff spike.

The final output in this form is directed from the integrator 195 over line 196 and indicates the magnitude and occurrence of true korotkoff sound signals in the time and blood pressure domains, as produced by the three channel waveform analysis performed upon all the incoming signal waveforms to the sphygmomanometer system. The latter electrical output from the integrator 195 is then digitized by a conventional analog to digital converter (not shown) to provide the pulse data in a suitable form for utilization by the digital processing subsystem 116 for further analysis, evaluation and computation in carrying out the measurement process.

An additional electrical subsystem is provided within the analog prescreening subsystem, to prevent distortion of the amplitude of the output pulses from the integrator 195, by preventing the piling up of additional low amplitude pulse contributions which may occur due to pulse ringing. Such a condition may conceivably be produced by continued integration by the integrator 195 of the lesser pulses passed by the spike amplitude analysis channel, to provide a misleading single high amplitude pulse output or a series of secondary pulses.

In this connection, the electrical output from the rectifier 184 is also directed over line 187 to a peak rectifier 188 whose output is, in turn, directed over line 189 as input to a discriminator latch 190. The discriminator latch 190 provides a "true" output over line 191 which is the second enabling input to the AND gate 178 and, hence, the latch 190 controls the spike channel gate 186 to effectively pass or block electrical output from the rectifier 184 to the integrator 195.

In addition, electrical output from the AND gate 178 is also directed over line 193 to condition the integrator 195. In this regard, the input over the line 193 causes the integrator 195 to discharge as soon as the output of the AND gate 178 goes "false", so that closing of the control gate 186 by the AND gate 178 will discharge the integrator 195 in preparation for integration of the next korotkoff pulse, rather than having the integrator remain at a high or saturated level.

The effect of a peak rectifier 188 and discriminator latch 190 on the integrator 195 is to provide a variable integration threshold for the integrator which effectively prevents the integrator from accepting and integrating smaller pulses for a period of time after a larger genuine korotkoff spike pulse has been accepted. The way in which this is accomplished is by varying the amplitude level of the pulses that can be passed by the control gate 186 under the control of the gate 178 which is, in turn, controlled by the state of the disciminator latch 190. In this regard, the variable threshold level is determined by the state of charge of a capacitor in the peak rectifier 188 which, as previously indicated, receives the output from the rectifier 184.

Figure 19A:
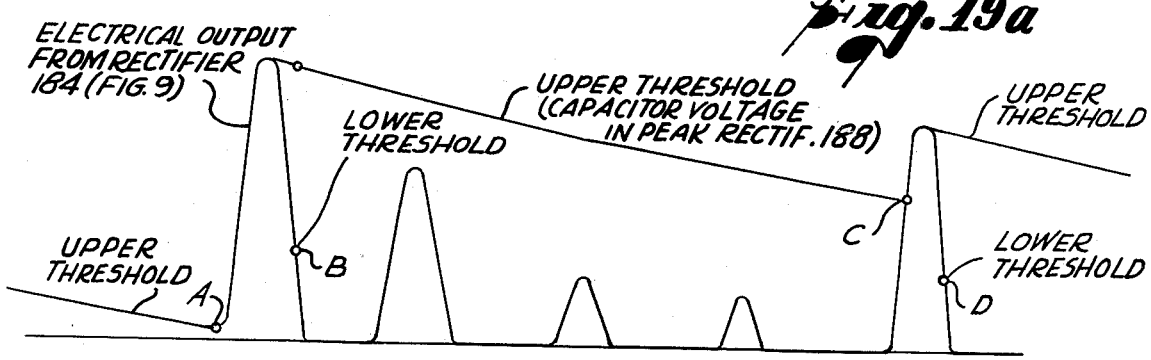
Figure 19B:
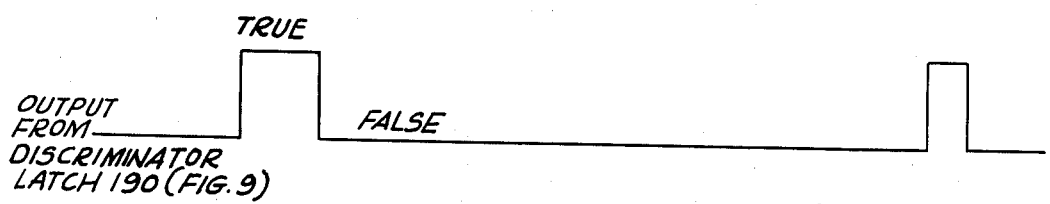

The operation of the peak rectifier 188 and discriminator latch 190 may be better understood by reference to FIGS. 19a and 19b, FIG. 19a representing the upper and lower amplitude thresholds imposed upon the control gate 186 and integrator 195 by the operation of the peak rectifier 188 and latch 190, while FIG. 9b indicates the corresponding output states of the discriminator latch 190.

The spike voltage output from the rectifier 184 in the spike amplitude analysis channel must be higher than the capacitor voltage of the peak rectifier 188 for the discriminator latch 190 to provide a "true" enabling output to the gate 178 and, hence, pass the output of the rectifier 184 to the integrator 195 through the control gate 186. As soon as the output from the rectifier 184 decays below a variable prescribed minimum threshold, e.g., one-third of the level of the capacitor voltage of the peak rectifier 188, the discriminator latch 190 is again disabled.

The spike waveforms shown in FIGS. 19a are the electrical output from the rectifier 184, whereas the koff sound signals first appear, prevention of over-inflation, initiation and control of deflation, as well as dumping of the remaining pressure in the cuff after sufficient information has been obtained to make all of the required blood pressure and heart rate determinations. This dumping of cuff pressure minimizes extended occlusion of the patient's artery beyond the time needed to complete the measurement process, particularly where the patient is being continuously monitored and the measurement process may be repeated on a frequent basis.

Control over inflation of the bladder 106a in the cuff 106 is effected by the processor subsystem 116 over line 117, which imposes control over the automatic air supply 107 so that the latter can be selectively turned on or off. In addition, the processor subsystem 116 controls the bleeder valve 111 by electrical input over line 118. The processor subsystem 116 receives the necessary information to effect such control over the air supply 107 and bleeder valve 111 by receiving electrical information from the pressure transducer 109 over line 119.

If it is desired to continuously monitor blood pressure in a patient by regular and repeated measurement cycles, an optional timer 120 may be used to provide additional timing information over line 121 to the processor subsystem 116. The processor subsystem can also provide information over line 122 to an optional display printer 123. The timer 120 and display printer 123 may be of conventional design.

Figure 7:
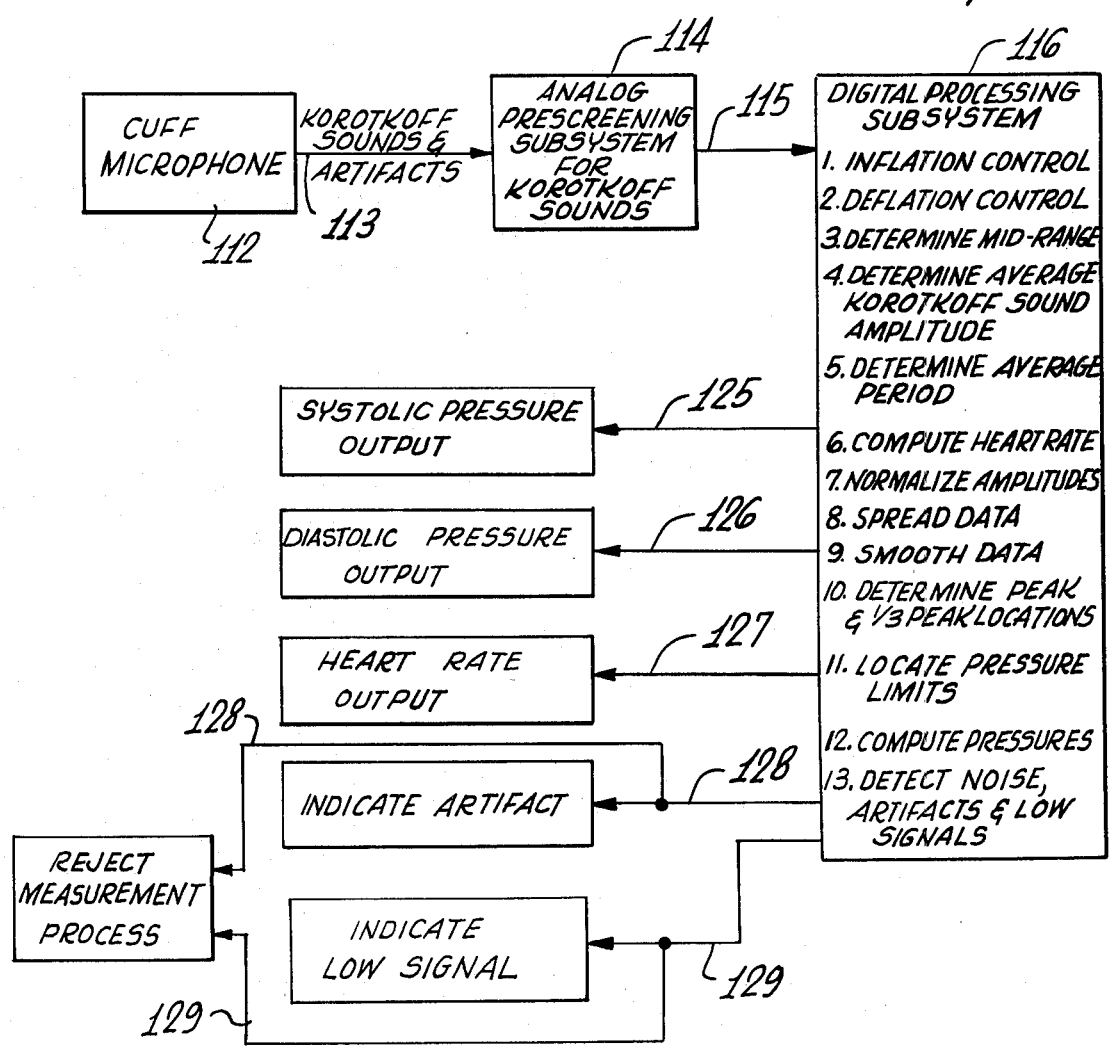
FIG. 7 is a block diagram of an overall sphygmomanometer analysis system in accordance with the invention.

FIG. 7 is a block diagram indicating in greater detail the overall sphygmomanometer analysis system, and, in particular, the functions performed by the waveform filter 114 and the processor subsystem 116.

The cuff microphone 112 directs electrical information over line 113 to the input of the waveform filter 114 which is an analog prescreening subsystem for separating true korotkoff sounds from artifacts and noise. The subsystem 114 provides prescreened output in the form of korotkoff pulses proportional in height to the amplitude of the korotkoff spikes and located in the time and blood pressure domains in correct correlation with the true korotkoff sound signals, over line 115 to the digital processing subsystem 116. In accordance with the invention, the digital processing subsystem 116 performs the following operations:

1. Inflation control including initiation and termination.
2. Deflation control including initiation, termination and dumping of cuff pressure.
3. Determination of the most highly reliable mid-range of the korotkoff sound pulse spectrum for analysis.
4. Determination of the average korotkoff sound pulse amplitude in the mid-range.
5. Determination of the average period between adjacent korotkoff pulses in the mid-range.
6. Computation of heart rate.
7. Normalization of the korotkoff pulse data to a standardized average for further analysis.
8. Spreading of the normalized data over adjacent channels.
9. Successive smoothing of the spread data to provide a digitized smoothed waveform.
10. Determination of the peak and ⅔ peak amplitude locations in the smoothed data.
11. Location of diastolic and systolic pressure limits in the smoothed data.
12. Computation of systolic and diastolic blood pressures.
13. Detection of noise and artifacts and low signals.

The digital processing subsystem 116, in performing the aforementioned functions, generates a plurality of outputs in accomplishing the measurement process. Systolic and diastolic blood pressure outputs are provided over lines 125 and 126, respectively, while the heart rate computed from the average korotkoff sound pulse period is provided as an output over line 127.

In the event the digital processing subsystem 116 determines that there are too many artifacts or too much noise in the data stream, so that the measurement process is not reliable, an output is provided over line 128 which indicates the presence of an "ARTIFACT" condition and the measurement process is rejected. Similarly, if the amplitudes of the korotkoff pulse stream are determined by the digital processing subsystem 116 to be too small for adequate reliability in the measurement process, then an output is provided over line 129 indicating the "LOW SIGNAL" condition and again, rejecting the measurement process. In this way, the overall sphygmomanometer system provides accurate output indicating blood pressure and heart rate when the data is determined to be reliable, and will not provide misleading output when the data is considered to be unreliable. In the latter instance, rejection of the measurement process by the system will normally inform the operator of the nature of the problem that the process should be repeated until reliable data is obtained.

Figure 8:
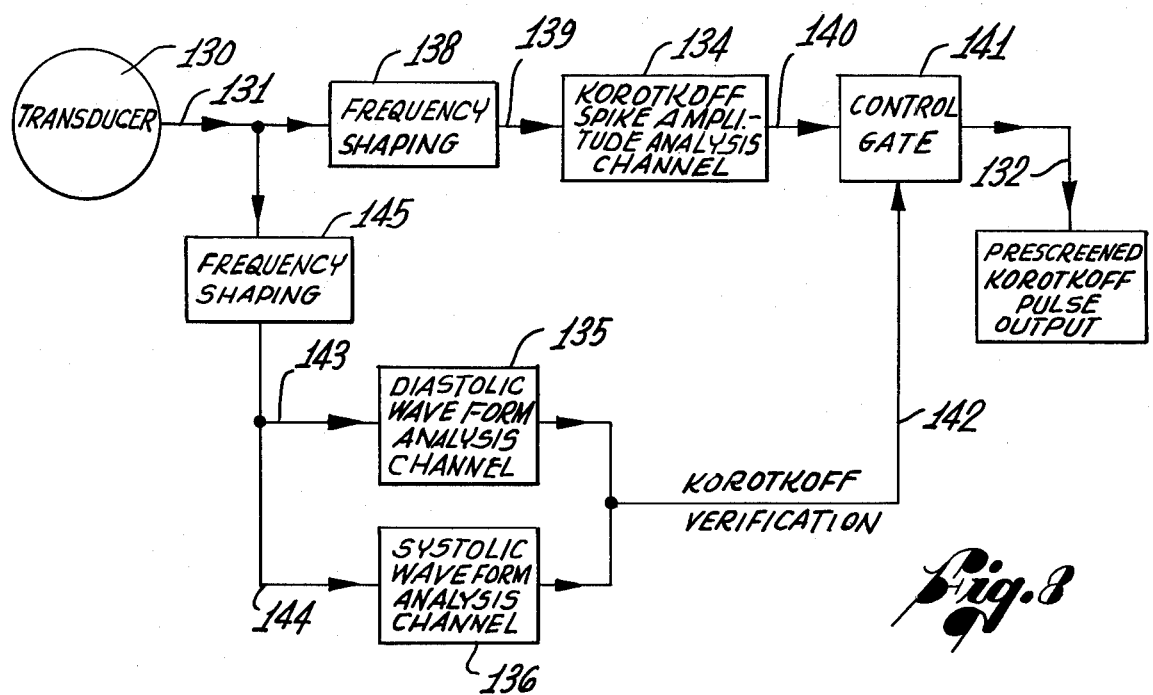
FIG. 8 is a block diagram of an analog prescreening subsystem for performing waveform analysis upon the incoming korotkoff sound signals.

Referring now more particularly to FIG. 8 of the drawings, there is shown a block diagram of an analog prescreening subsystem for performing waveform analysis upon the incoming korotkoff sound signals. In accordance with the invention, auscultatory korotkoff sounds are detected by a microphone transducer 130 and directed as electrical signal input over line 131 to a three-channel analog prescreening subsystem which filters the incoming signal and ultimately provides, as electrical output over line 132, a pulse train correctly correlating and marking the locations of true korotkoff sound signals in the time and blood pressure domains, with each output pulse being proportional in amplitude to the corresponding korotkoff sound signal represented.

Figure 1A:
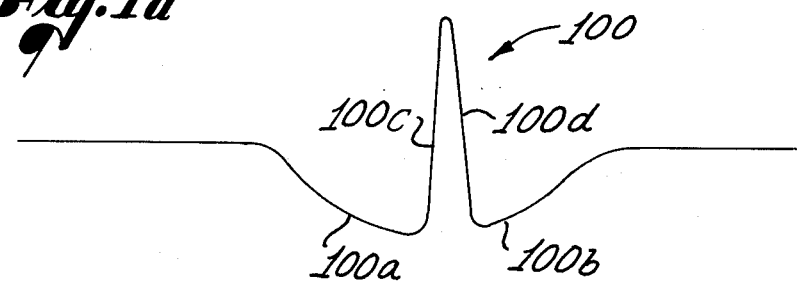
FIGS. 1a and 1b illustrate idealized waveforms representing the interaction of pulsating blood pressure and cardiovascular physiology resulting in the production of korotkoff sound signals during cardiac cycles.
Figure 1B:
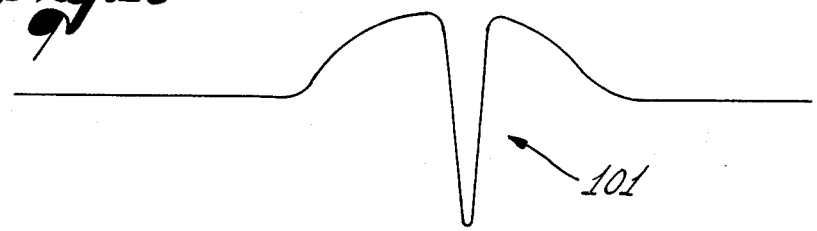
Figure 2:
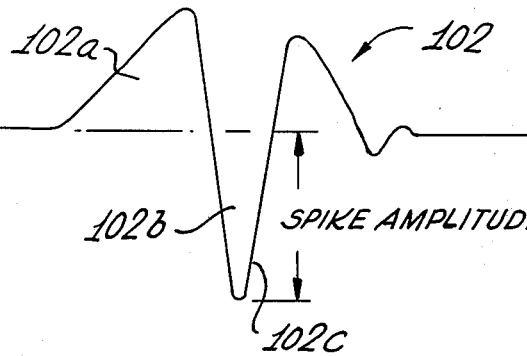
FIG. 2 illustrates a generalized representation of a class of korotkoff sound signal waveforms detected by a microphone, in accordance with the invention, typically encountered in the diastolic blood pressure region and, at times, in the systolic blood pressure region as well.
Figure 3:
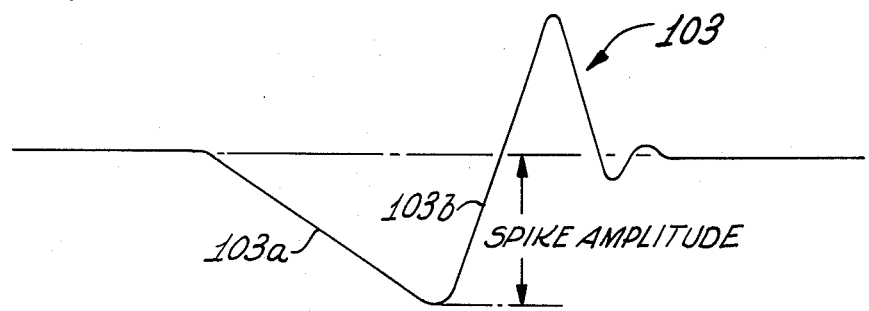
FIG. 3 illustrates a generalized representation of a class of korotkoff sound signal waveforms sometimes encountered in the systolic blood pressure region of the korotkoff sound signal stream.

The analog prescreening subsystem of FIG. 8 performs waveform analysis upon all of the incoming signal waveforms, based upon the discovery of certain unique characteristics associated with those waveforms correctly depicting true korotkoff sound signals, and particularly the previously described waveforms 102 and 103 shown in FIG. 2, and FIG. 3, respectively, in contrast with those waveforms representing a variety of artifact and noise signals. In this connection, it has been discovered in the course of the present invention that waveform characteristics of the incoming signals, as opposed to frequency characteristics only, provide the most reliable means for accurately separating korotkoff sound signals from an electrical signal environment which also includes artifact and noise signals falling within the same frequency domain normally associated with true korotkoff sound signals.

The analog prescreening subsystem of FIG. 8 includes three analysis channels for processing all incoming signal waveforms, a korotkoff spike amplitude analysis channel 134 to measure the amplitude of the korotkoff sound signal and produce an output pulse proportional to that amplitude, a diastolic waveform analysis channel 135 which correlates the incoming signal waveform with the generalized diastolic waveform 102 (FIG. 2) to indicate the occurrence of a true korotkoff sound signal, and a systolic waveform analysis channel 136 which correlates all of the incoming signal waveforms with the generalized systolic waveform 103 (FIG. 3) to likewise certify the occurrence of a true korotkoff sound signal.

Figure 4:
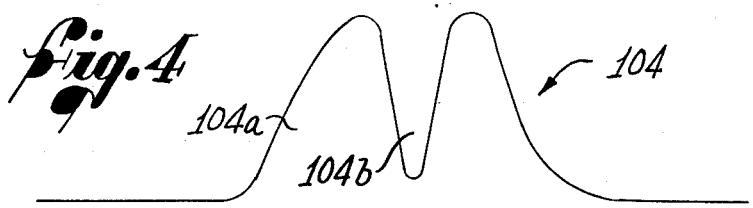
FIG. 4 illustrates a generalized korotkoff signal waveform showing a spike signal phase masked by relatively high level, low frequency positive signal component contribution.
Figure 5:
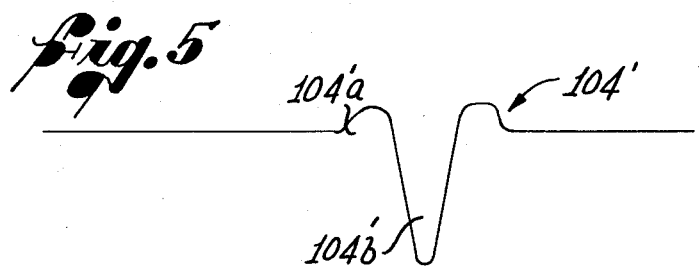
FIG. 5 illustrates the waveform of FIG. 4 modified by frequency shaping in the system of the present invention.

In the korotkoff spike amplitude analysis channel 134, the incoming signal waveform over line 131 first undergoes preliminary frequency shaping via a frequency shaping network 138 to establish a frequency domain for accepted signals between approximately ½ Hz. and 150 Hz. However, the region between ½ Hz. and approximately 5 Hz. is attenuated relative to the region between approximately 15 Hz. and 150 Hz. so that the primary frequency range is the latter, 15 Hz. to 150 Hz. range, but some low frequency signal is permitted to leak through to provide the types of waveform modification illustrated in converting the waveform 104 in FIG. 4 to the modified waveform 104' in FIG. 5.

The frequency shaped signal from the network 138 is directed over line 139 to the spike analysis channel 134 which ultimately provides the required pulse output correlated with the occurence of true korotkoff sound signals in the input, sensed by the transducer 130.

The electrical output from the spike analysis channel 134, appearing on line 140, cannot be passed as prescreened korotkoff pulse output unless a control gate 141 is first enabled by a "TRUE" korotkoff verification signal received over line 142 as a control input from one or both of the diastolic and systolic analysis channels 135, 136, respectively. Hence, the amplitude and time correlated pulses produced by the spike amplitude analysis channel 134 will normally be blocked from appearing as electrical output over line 132 from the analog prescreening subsystem unless the spike channel control gate 141 is simultaneously opened by a verified true korotkoff signal output from either the diastolic analysis channel, the systolic analysis channel, or both. In this latter regard, signal waveforms may occur in the incoming data which possess waveform characteristics acceptable to both systolic and diastolic analysis channels, or acceptable to only one of them, but a "TRUE" output from either analysis channel over line 142 is sufficient to gate "ON" the prescreened korotkoff pulse output from the spike channel over line 132, so that they can be passed on to the digital processing subsystem 116 for further analysis, evaluation, verification, and computation.

The incoming signal waveforms to the diastolic and systolic waveform analysis channels also undergo frequency shaping prior to being inputted to the analysis channels over lines 143 and 144. This is accomplished in a frequency shaping network 145 which removes extremely low frequency and high frequency artifact and noise signals and provides an acceptance region of approximately ½ Hz. to 15 or 20 Hz. in the frequency domain.

Figure 9:
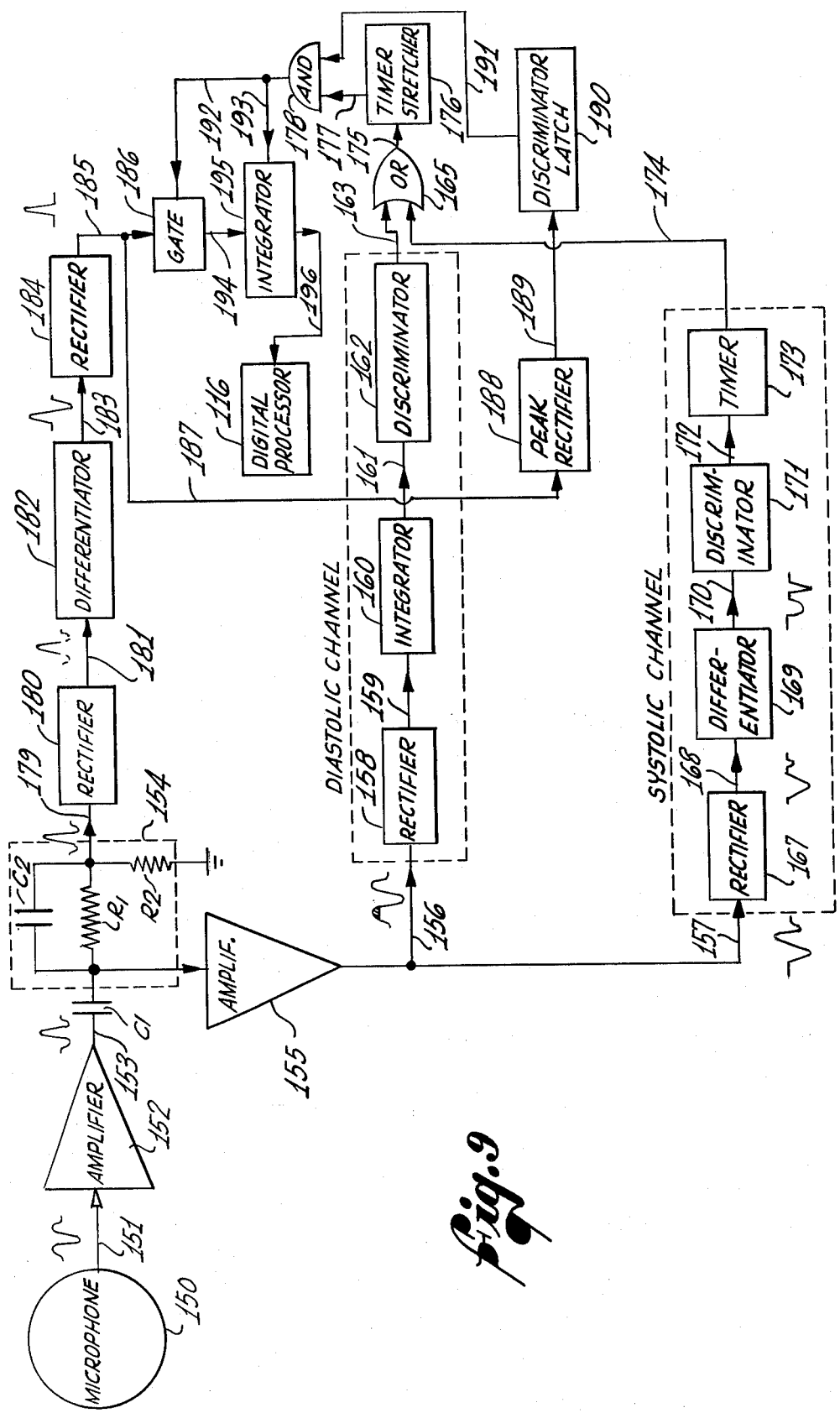
FIG. 9 is a combined block diagram and electrical schematic of a presently preferred embodiment of an analog prescreening subsystem in accordance with the present invention.

Referring now to FIG. 9 of the drawings, there is shown a combined block diagram and electrical schematic of a presently preferred embodiment of an analog prescreening subsystem in accordance with the present invention. Waveforms are shown at various places in FIG. 9 to facilitate a greater understanding of the functions being performed by the various subsystem components.

The korotkoff sounds in the cuff are sensed by a microphone 150 to produce corresponding electrical signal input over line 151 to an inverting preamplifier 152. A variety of different microphone transducers may be utilized in the practice of the invention to perform the fuctions of the microphone 150. In this regard, however, a microphone 150 of the piezoelectric type, and sold under the brand name "UNIMORPH" as part No. 60708, made by Vernitron Piezoelectric Division, 232 Forbes Rd., Bedford, Ohio, has proven to be particularly suitable in practicing the invention and in providing the type of response characteristics which yield proper korotkoff sound waveforms.

The inverted electrical output from the amplifier 152 is directed over line 153 through a coupling capacitor C1 as input to the spike amplitude, diastolic and systolic waveform analysis channels.

In the spike amplitude analysis channel, the incoming signal waveform first undergoes preliminary frequency shaping by a frequency network 154 comprising a pair of resistors R1 and R2, with a shunt capacitor C2 shunting the resistor R1. The frequency shaping network 154 establishes a frequency domain for accepted signals between approximately ½ Hz. and 150 Hz. with 6 db per octave rolloff beyond the upper limit of 150 Hz. However, the region between ½ Hz. and approximately 5 Hz. is attenuated relative to the region between approximately 15 Hz. and 150 Hz. so that the primary frequency range is in the latter 15 Hz. to 150 Hz. range, but with some low frequency signal deliberately permitted to leak through to the input of the spike channel. Hence, while low frequency noise and artifact signals are substantially attenuated, sufficient low frequency is present to translate the position on the korotkoff spike to the opposite side of the time axis from the precursor bulge, so that the amplitude of the korotkoff spike is positioned on the appropriate side of the axis for proper amplitude analysis by the balance of the spike amplitude analysis channel.

Figure 11:
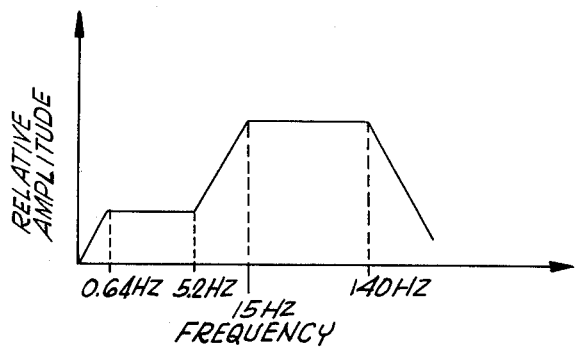
FIG. 11 illustrates the frequency characteristic for another portion of the analog prescreening subsystem shown in FIG. 9.

FIG. 11 illustrates the frequency characteristic for the frequency shaping network 154 shown in FIG. 9. The frequency values indicated in the characteristic are presently preferred values, although it has been found that the upper frequency range may be extended from 15 or 20 Hz. at the low end to approximately 150 Hz. at the upper end, with the secondary, low frequency range, extending from ½ Hz. to as much as 10 Hz. The rolloff characteristics between the upper frequency range and the lower frequency range is not critical, but the rolloff below ½ Hz. is approximately 6 db per octave to eliminate extremely low frequency artifacts.

The incoming signal waveforms from the amplifier 152 also undergo amplification and frequency shaping in the amplifier 155 prior to being passed as re-inverted input over lines 156 and 157 to the diastolic and systolic waveform analysis channels, respectively. The frequency shaping which is accomplished by the amplifier 155 removes extremely low frequency and high frequency artifacts and noise signals and provides an acceptance region of approximately ½ Hz. to 15 or 20 Hz. in the frequency domain, with rolloff at both ends of the frequency spectrum of approximately 6 db per octave.

Figure 10:
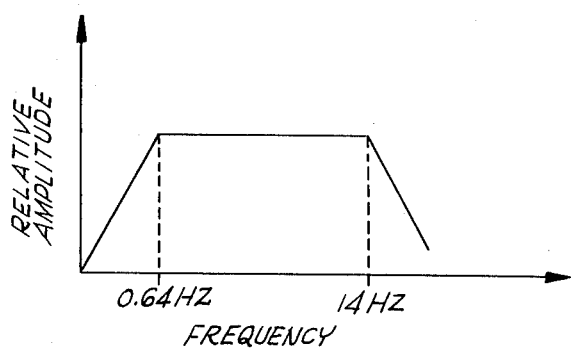
FIG. 10 illustrates the frequency characteristics for one portion of the analog prescreening subsystem shown in FIG. 9.

The frequency characteristic for the frequency shaping amplifier 155 is illustrated in FIG. 10 of the drawings. The particular values of frequency at the low and high ends of the pass band shown in FIG. 10 are presently preferred values, although the pass band may be upper threshold envelopes superimposed upon the series of pulse waveforms represents the capacitor voltage in the peak rectifier 188. Assuming that the peak rectifier capacitor has decayed to a very low level and, hence, the upper threshold level is at its lowest value, the discriminator latch 190 output goes positive at point A on the leading edge of the pulse output from the rectifier 184. Since the discriminator latch 190 is now positive, the gates 178 and 186 are both enabled to pass the output of the rectifier 184 to the integrator 195 in the output stage of the spike amplitude and analysis channel.

As the electrical output from the rectifier 184 falls, on the trailing edge of the first large spike in FIG. 19a, the minimum lower threshold value is passed at point B, which causes the discriminator latch 190 to go "false" and thereby disable the gates 178 and 186 to block output from the rectifier 184 to the integrator 195.

Since the next three voltage spikes in FIG. 19a provided as output from the rectifier 184, as might be produced by ringing on the line, fail to rise to the upper threshold level now established by the decaying capacitor voltage in the peak rectifier 188, the latch output remains "false" and the spike channel control gate 186 remains closed. However, the fifth spike from the rectifier 184, representing a true korotkoff sound signal, exceeds the upper threshold limit at point C to again drive the discriminator latch output positive, to charge up the capacitor in the peak rectifier 188, and again reset the upper threshold level to a higher magnitude from which it will gradually decay. As in the case of the previous true korotkoff pulse, when the voltage output from the rectifier 184 falls below the lower threshold which is typically some small fraction of the capacitor voltage in the peak rectifier 188, as at point D, the latch output again goes "false" and the spike channel control gate 186 is again disabled.

Hence, since the integrator 195 can only operate when the output of the discriminator latch 190 is positive, it will be apparent that the peak rectifier 188 and latch 190 effectively operate upon the control gate 186 to prevent the integrator from accepting and integrating smaller pulses for a period of time after the larger genuine korotkoff spike has been accepted.

Figure 17:
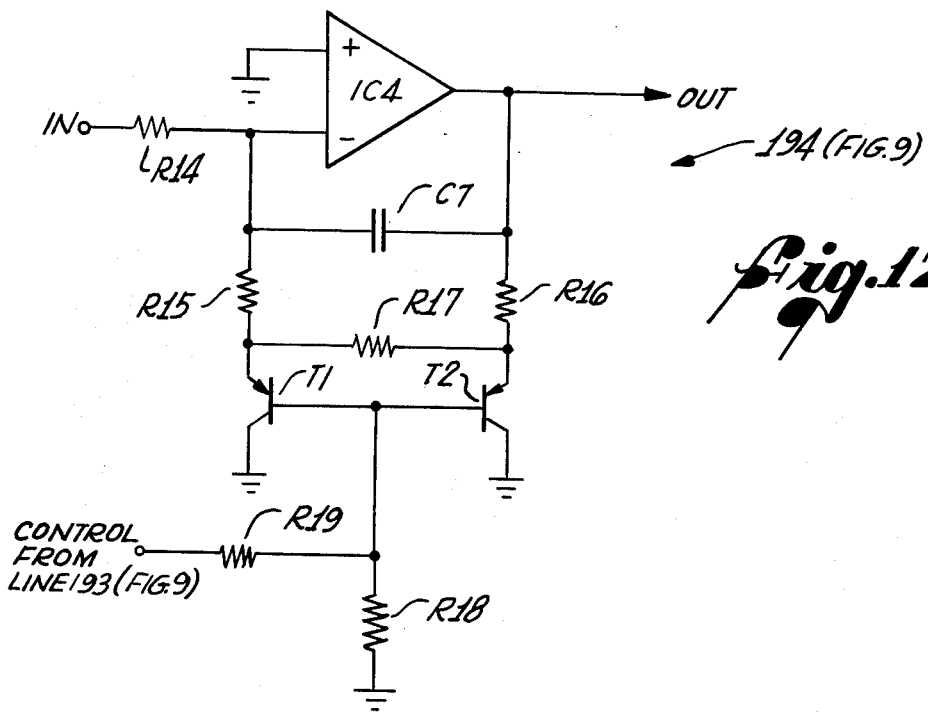
FIG. 17 is an electrical schematic diagram for one embodiment of an output integrator stage suitable for use in the analog prescreening subsystem of the invention.

One example of electrical circuitry suitable for performing the functions of the integrator 195 is shown in FIG. 17, wherein:
R14=4.7 kilohms
R15=4.7 kilohms
R16=4.7 kilohms
R17=1.0 kilohms
R18=10 kilohms
R19=10 kilohms
C7=0.33 microfarads
T1=T2=Type 2N3638A
IC4=LM324 manufactured by National Semiconductor Corp.

One embodiment of electrical circuitry suitable for performing the functions of the peak rectifier 188 and discriminator latch 190 is shown in FIG. 18, wherein:
R20=1.0 kilohms
R21=100 kilohms
R22=47 kilohms
R23=10 kilohms
R24=10 kilohms
R25=10 kilohms
R26=15 kilohms
C6=1.0 microfarads
CR5=CR6=CR7=Type 1N4148
B+=+5 volts
IC5=LM324 manufactured by National Semiconductor Corp.
IC6=IC7=IC8=LM339 manufactured by National Semiconductor Corp.

Figure 36:
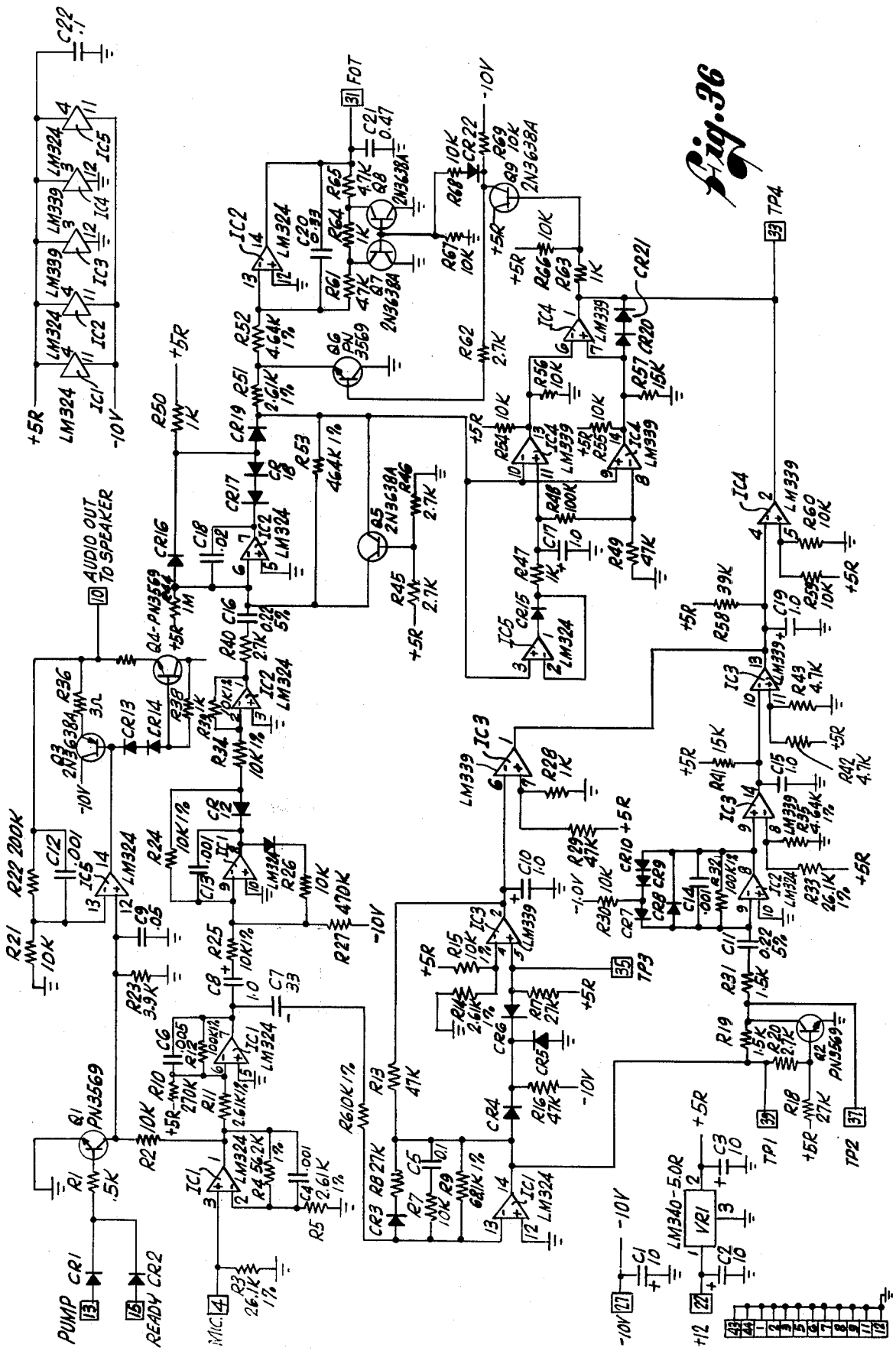

While the structure and operation of the analog prescreening subsystem shown in FIG. 9 has been disclosed in sufficient detail to enable one having ordinary skill in the art to make and practice the invention, a further more detailed electrical schematic of suitable circuitry is provided for convenience and is attached hereto as FIG. 36.

The digital processing subsystem 116 in FIG. 9, in accordance with the invention, not only performs further analysis upon the korotkoff sound pulse stream output from the integrator 195 of the analog prescreening subsystem, but also performs other control functions relating to start-up of the sphygmomanometer system and conditioning of the system to enable the measurement process to proceed. This includes, by way of example, control of the inflation of the cuff upon the arm of the patient, determination that the inflation has reached a proper level to enable proper data to be obtained, prevention of over-inflation, and initiation and control of deflation, as well as dumping of the remaining pressure in the cuff after sufficient information has been obtained to make all of the required blood pressure and heart rate determinations. These functions were described generally in connection with the previous discussion for the digital processing subsystem 116 in FIG. 7 and will now be elaborated in greater detail.

Figure 20:
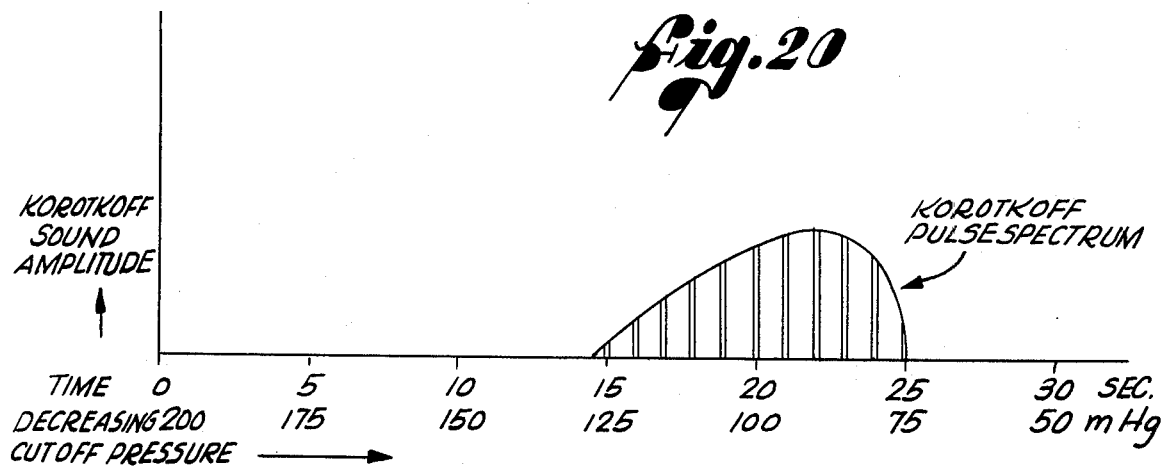

Referring now to FIG. 20, there is shown a graphical representation of typical korotkoff sound signal pulse amplitudes produced at the output of the integrator 195 from the analog prescreening subsystem in FIG. 9, for use by the digital processing subsystem 116. FIG. 20 shows a typical series of korotkoff pulses as represented by the illustrated pulse spectrum, each individual pulse representing a corresponding korotkoff sound signal amplitude in the time and pressure domains. The pressure is shown as going from a high level to a low level from left to right, with time increasing in the same direction, so that the korotkoff pulse spectrum represents the korotkoff signals detected during a deflation process which occurs typically at a deflation rate of approximately 5 mm. Hg per second.

Figure 21:
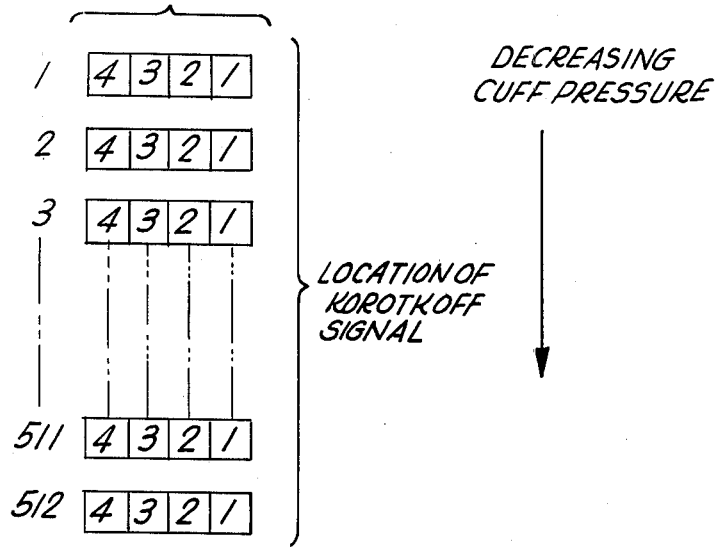

For purposes of convenience, the korotkoff pulses shown in FIG. 20 are stored in a shift register memory in the digital processing subsystem, and the location in that shift register memory is representative both of the time of occurrence and timing between the korotkoff pulses, as well as of the actual pressure in the inflated cuff at the time that the corresponding korotkoff sounds appeared. In this regard, FIG. 21 schematically illustrates the data storage register for recording the location and amplitude of korotkoff sound signal pulses provided as output from the analog prescreening subsystem and consists of 512 4-bit positions. Each of the 512 positions is capable of storing one korotkoff pulse amplitude and corresponds to a particular cuff and blood pressure, the actual magnitude of the blood pressure represented by any particular position in the register depending upon the magnitude of the starting pressure and when the first korotkoff sound signals appear.

Assuming a difference in blood pressure of ½ mm. Hg between adjacent positions in the shift register, the 512 positions cover a blood pressure range of approximately 256 mm Hg. Each location in the shift register of FIG. 21 represents an absolute pressure even though, in each measurement cycle, a particular shift register location may not be dedicated to the same pressure because of the difference in starting pressure and the time of occurrence of the first korotkoff pulse. In addition, the shift register is continually stepped as the deflation process occurs, and a korotkoff pulse will not be stored in every shift register location.

The selection of 4-bits at each shift register location, to designate pulse amplitude, is merely a matter of choice, the 4-bit code being a logarithmic code for economy of storage space. However, any suitable number of bits and digital code may be used to store the value of pulse amplitude at each shift register location.

Figure 22:
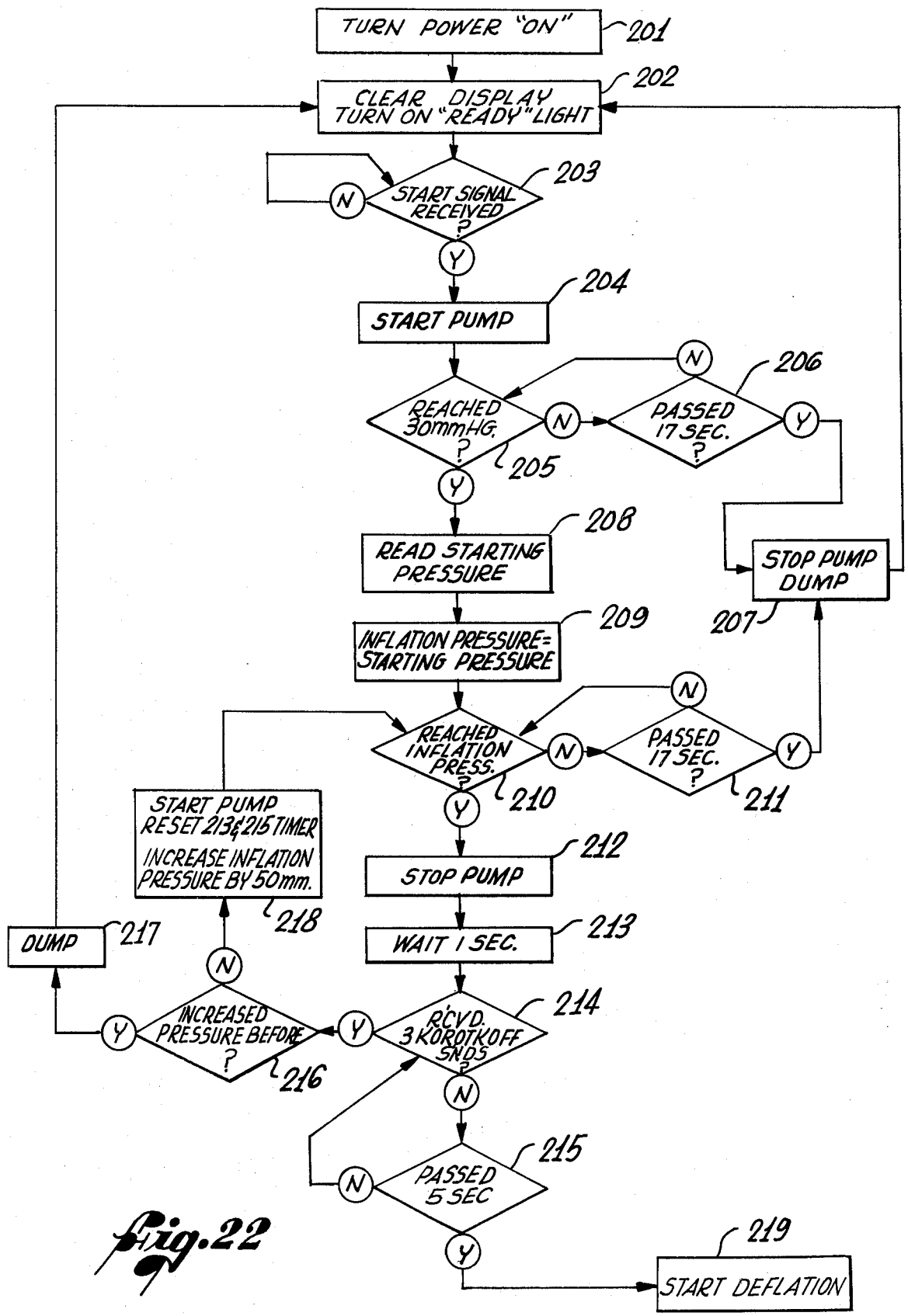

FIG. 22 is a flow chart illustrating the start up process for inflation and deflation by the digital processing system.

In step 201, system power is turned "on" and the next step 202 clears the display system, turns on the "ready" light to indicate to the operator that the system is ready to initiate the measurement cycle, and the analog-to-digital converter used to digitize the korotkoff pulse output stream from the prescreening subsystem to the digital processing subsystem is cleared and reset to zero. Step 203 checks for the presence or absence of an internally generated "start" signal. The process does not proceed further until the "start" signal is finally received. When the "start" signal has been received, the automatic air pump under the control of the digital processing subsystem is started, to inflate the cuff on the arm of the patient, and typically an "inflate" light will be energized to again inform the operator of the particular stage of the measuring process taking place.

After the inflation process has started in step 204, the pressure is checked at 205 to determine whether or not the pressure has reached a first benchmark level of 30 mm. Hg. If the latter pressure has not yet been reached, the question is asked at 206 whether or not 17 seconds have elapsed. If the answer is no, the system recycles to test 205 to again determine whether or not 30 mm. Hg has been reached and, if not, again asks question 206 to determine whether or not it is taking more than 17 seconds to reach 30 mm. Hg pressure. If the system does not reach 30 mm. Hg within 17 seconds, then the answer to question 206 is yes, and the system proceeds to step 207 which stops the pump and dumps the air pressure from the cuff to abort the measurement process, since apparently some malfunction has occurred, such as a leak in the cuff. Step 207 also returns the system to step 202, after dumping the pressure in the cuff, to place the system in the "ready" state for beginning a new measurement cycle.

If the answer to question 205 is yes, i.e., 30 mm. Hg is reached in less than 17 seconds, the inflation process continues to step 208 where the system reads the starting pressure which is typically selected by means of a variable pressure switch or the like (not shown).

Step 209 continues the inflation process in an attempt to reach the selected starting pressure. In step 210, the question is asked whether or not the inflation pressure has reached the starting pressure. If the answer is no, the question is asked at 211 whether or not 17 seconds have passed and, if not, the inflation pressure is again tested at 210, until either 17 seconds have elapsed or the inflation pressure has in fact reached the prescribed pressure level. If 17 seconds do elapse before the inflation pressure has reached a sufficient level, then the answer to question 211 is yes, indicating some inflation problem exists and, therefore, step 207 is again initiated to stop the pump, dump the air pressure in the cuff, and return the system to the "ready" state for a new measurement cycle in step 202.

If the answer to question 210 is yes, indicating that the proper inflation pressure has been reached in less than 17 seconds, the pump is turned off in step 212 and the system waits for one second in step 213 after turning off the pump. The next procedure, carried out in steps 214 and 215, essentially determines whether or not more than two korotkoff sound signals have been detected in the next five second period. In this regard, receipt of three or more korotkoff sounds within the five second period would typically indicate that the system had not inflated the cuff to a high enough pressure above the systolic blood pressure level, since the system had apparently entered the korotkoff region at the selected starting pressure. On the other hand, if less than three korotkoff sounds are received in a five second period, the system assumes that the starting pressure was sufficiently high above the systolic region to warrant initation of the deflation process. The occurrence of two or less pulses in a five second time period is too infrequent to be characteristic of true korotkoff sound signals and, therefore, would typically represent noise or artifact signals and would be ignored by the system in determining whether or not the deflation process should be initiated. Hence, if the answer to question 214 is no, question 215 determines whether or not five seconds have elapsed and, if not, the system returns to step 214 to listen further for korotkoff sound signals until the five second period is completed.

If the answer to question 214 is yes, indicating that the pressure is not high enough, because of receipt of korotkoff pulses, then step 216 determines whether or not the inflation limit has been increased before. If the inflation pressure limit has not been increased before, the system proceeds to step 218 which restarts the pump, resets the timing systems for steps 213 and 215 and increases the inflation pressure limit by 50 mm. Hg to return the system to step 210 which then continues the inflation process until the inflation pressure reaches the newly established inflation pressure limit.

If the answer to question 216 is yes, indicating that the pressure limit had been increased once before, the system dumps the cuff pressure via step 217 and returns to the "ready" state in step 202 for beginning of a new measurement cycle. The reason for this is to indicate to the operator that the system would call for pumping up the cuff on the arm of the patient to a rather high level, i.e., 100 mm. or more above the initial starting pressure selected by the operator. The operator can then investigate to determine whether or not it would be wise to repeat the measurement cycle with a higher initial starting pressure or whether the patient and environment are producing too many artifacts and noise signals causing the system to make a false determination at step 214 that higher inflation pressures are necessary.

Figure 6:
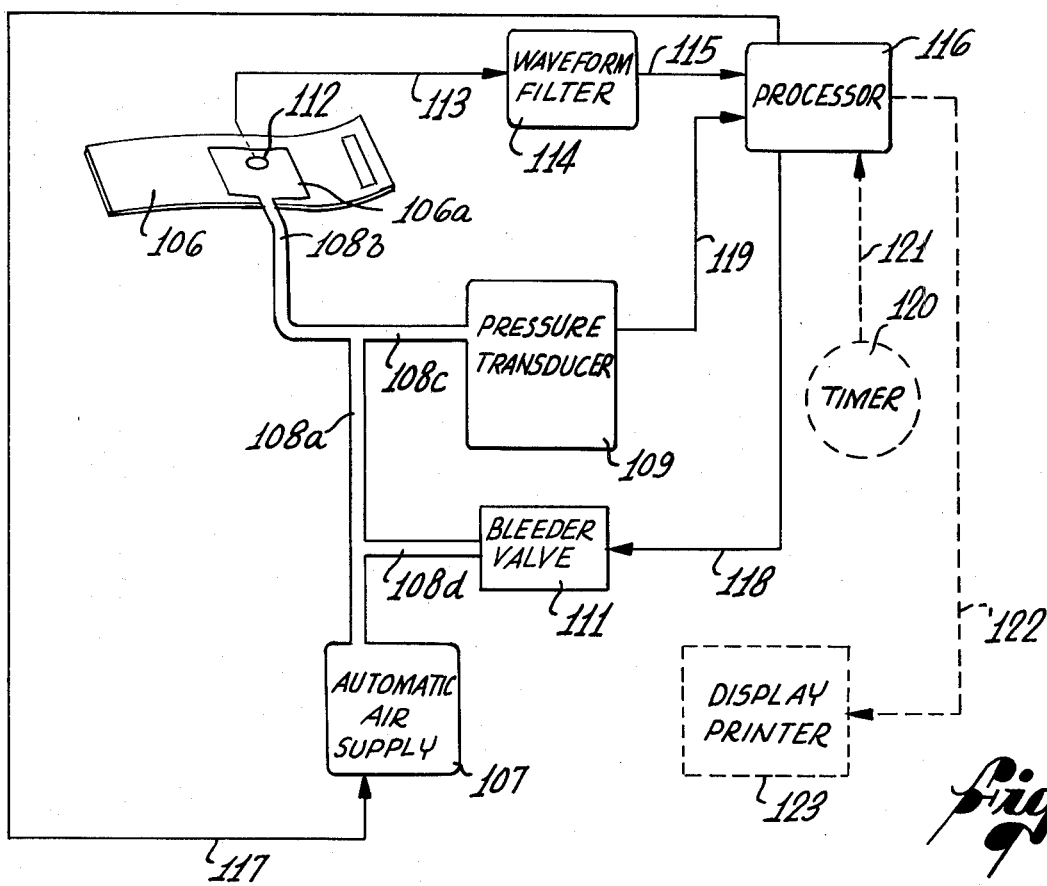
FIG. 6 is an overall block diagram of a generalized sphygmomanometer system incorporating features of the present invention.

If the five seconds elapses in step 215 with receipt of less than the three signal pulses, the deflation process is initiated in step 219. Typically, the deflation process involves automatic bleeding of air from the cuff at a prescribed rate, typically 5 mm. Hg per second, under the complete control of the digital processing system 116. By way of example, this procedure is illustrated in FIG. 6, previously discussed, wherein the processor 116 controls the bleeder valve 111 while monitoring the pressure in the cuff as measured by the pressure transducer 109.

Figure 23:
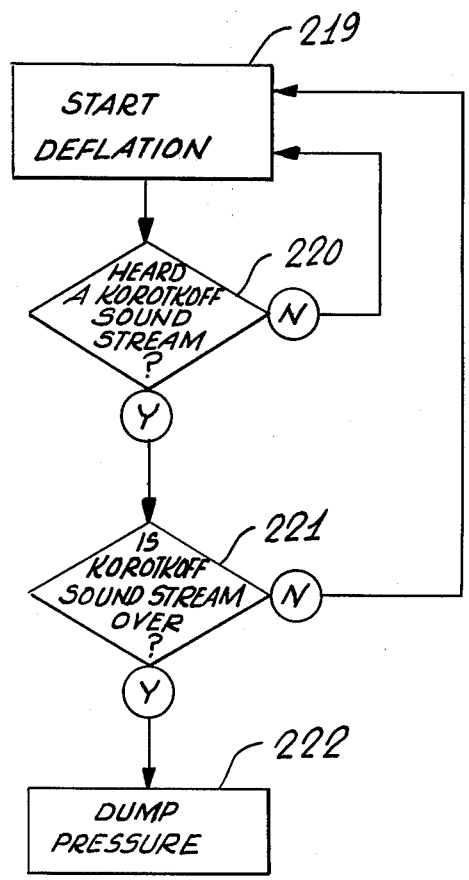

FIG. 23 is a flow chart illustrating the deflation process and, particularly, the dump detection procedure as implemented by the digital processing subsystem. In step 219, the aforementioned deflation process is carried out and, of course, all of the detected korotkoff sound signals received during the deflation process are written into the storage register previously discussed in connection with FIG. 21.

In step 220, a determination is made as to whether or not the system has detected any korotkoff sound signals as yet, and if the answer to question 220 is no, the deflation process is continued in step 219. If the answer to question 220 is yes, indicating that korotkoff sound signals have been received, a second question is posed at 221 to determine whether or not the korotkoff sound signal pulse stream is over. This can, of course, be accomplished by various timing tests (not shown) to indicate that a prescribed period of time has elapsed since the last korotkoff sound signal was heard. If the answer to question 221 is no, indicating that the korotkoff pulse stream is still continuing, then the deflation answer to question 221 is yes, indicating that the korotkoff pulse stream has passed and the system is now below the diastolic region, does the system proceed to step 222 which dumps the remaining cuff pressure.

The dumping of cuff pressure minimizes the extent of occlusion of the patient's artery beyond the time needed to complete the measurement process and is, therefore, particularly desirable in those situations where continuous monitoring and repetition of the measuring process is to be carried out. At this point in the overall process, with the completion of the deflation and dumping procedures, the digital processing subsystem 116 has received all of the korotkoff signal information and the stored data can now be acted upon for extraction of the desired measurement determinations regarding heart rate and blood pressure.

The first data manipulation performed in a digital processing subsystem, in accordance with the present invention, is selection of the most reliable range in the korotkoff sound pulse stream shown in FIG. 20, to determine what is referred to as the "mid-range". This is essentially accomplished by spreading and averaging the pulse amplitudes in groups, to locate the peak amplitude and mark the locations of the one-half-peak amplitudes on both sides of the maximum peak, the mid-range region being defined as the region extending between the two half-peak amplitude locations.

For purposes of determining the mid-range, it will be apparent that a smoothing operation is performed on the korotkoff pulses stored in the shift register memory. However, at this point, the korotkoff pulse data remains unchanged and is still stored in the shift register memory such as that previously discussed in connection with FIG. 21, in the original form it was received from the prescreening subsystem, the mid-range determination having no effect upon the actual data except the establishment of the most reliable range for further computation and examination.

Figure 24:
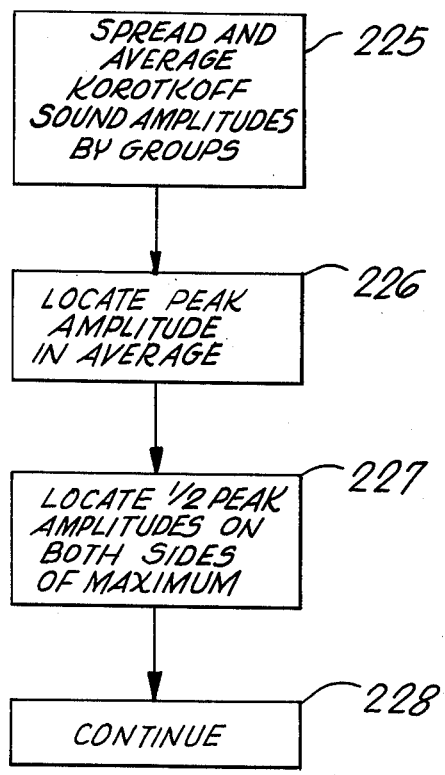

FIG. 24 is a flow chart illustrating the mid-range determination procedure implemented by the digital processor subsystem 116. In step 225, each of the korotkoff pulses is individually spread over a prescribed width of memory locations and, if any overlap occurs, the larger amplitude is retained. Then the amplitudes are averaged over a larger channel width and the location of the peak amplitude is determined in step 226. In step 227, the locations of the half-peak amplitudes both above and below the location of the peak are determined and stored in memory, and the system then continues its evaluation at 228.

Figure 25:
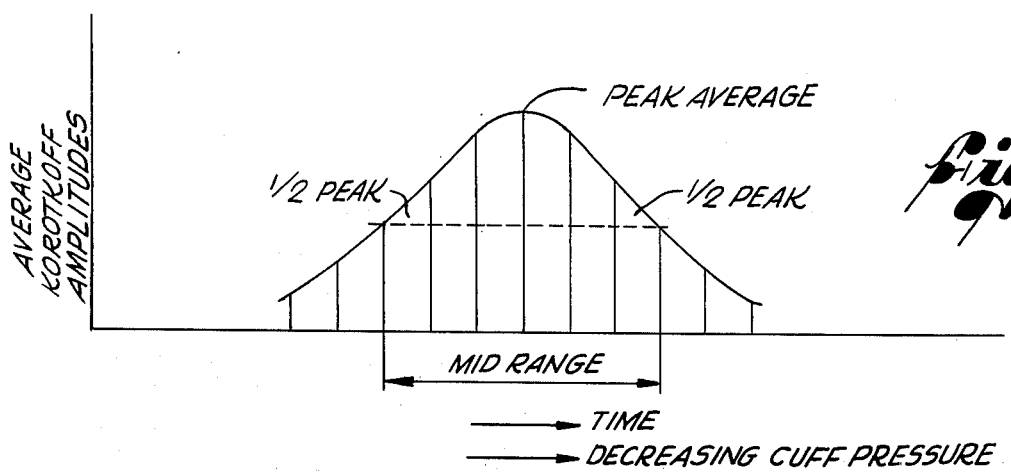

The mid-range process is graphically illustrated in FIG. 25 which shows the smooth data and the determination of the peak average and half-peak average locations defining the mid-range.

Figure 26:
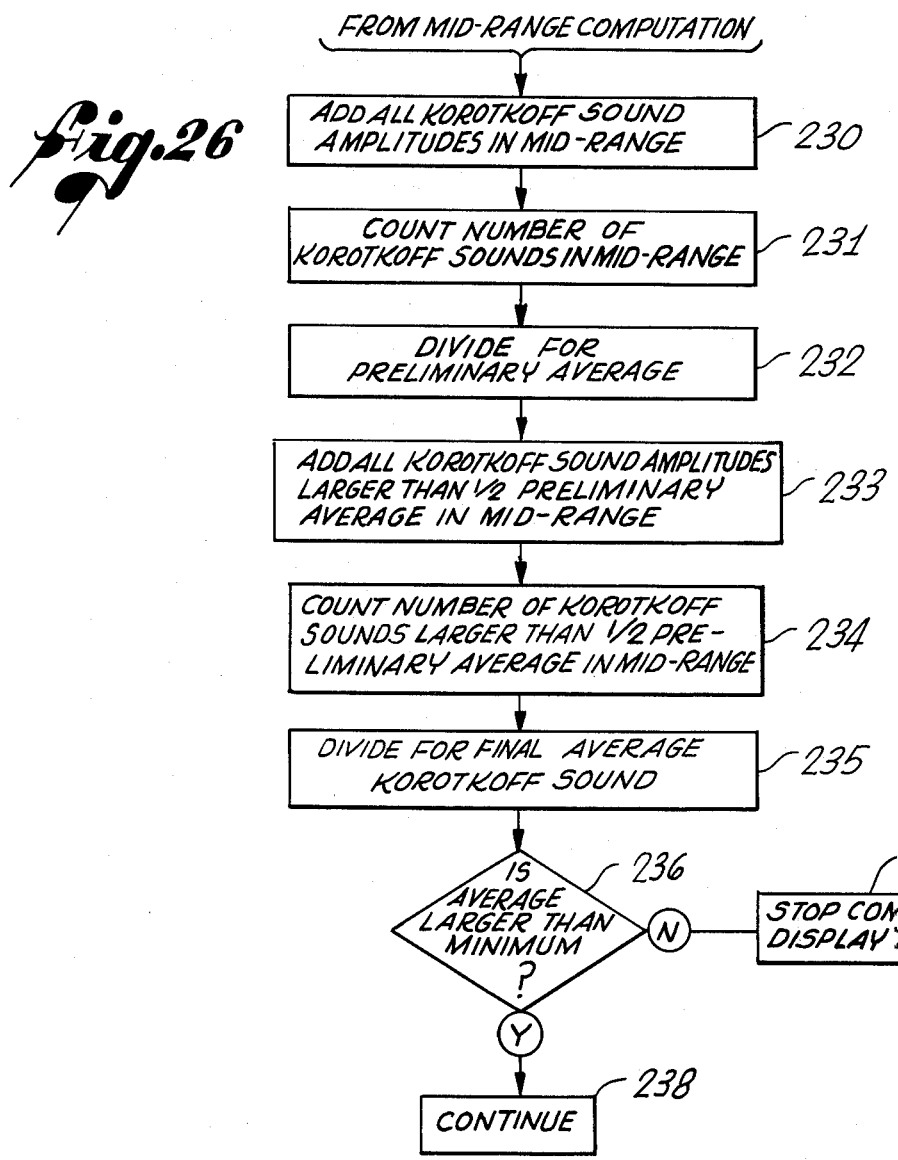

Once the mid-range determination has been made, the next procedure performed by the digital processing subsystem of the present invention involves the determination of the average amplitude of the korotkoff sound pulses within that mid-range region. In this regard, FIG. 26 is a flow chart illustrating the average korotkoff sound signal amplitude determination as implemented by the digital processing subsystem.

Initially, in step 230, all korotkoff sound signals in the mid-range are added. In step 231, the number of korotkoff sound signals in the mid-range is counted. In step 232, the amplitudes from step 230 are divided by the number of korotkoff sounds counted in the mid-range in step 231, to determine a first preliminary average for korotkoff sound amplitude.

This averaging process is then repeated, after first ignoring all amplitudes smaller than one-half of the average amplitude determined in the first averaging process, and a new average is thereby computed which serves to eliminate the contributions to the averaging process of low amplitude noise spikes and artifacts. In this regard, step 233 calls for adding all of the korotkoff sound amplitudes larger than one-half of the preliminary average in the mid-range, followed by a count of the number of korotkoff sound signals larger than one-half of the preliminary average, in step 234. In step 235, the final average amplitude for korotkoff sound signals in the mid-range is determined.

At step 236, a test is imposed to determine whether or not the final average amplitude computed is larger than a prescribed minimum. If the answer to question 236 is no, computation is stopped by a step 237 which also displays a "low signal" to the operator indicating that the signal data is too low in amplitude to be reliable, and the measurement process should be repeated.

If the answer to question 236 is yes, indicating that the average korotkoff sound amplitude is above a prescribed minimum, then the digital processing system continues its analysis via step 238.

The next procedure performed by the digital processing subsystem involves the determination of the average pulse period in the mid-range region. Again, the average period is first determined between the highest and lowest korotkoff sound pulses, i.e., between the half-peak amplitude korotkoff pulses defining the mid-range region. This average is then recomputed after first ignoring the contribution of those pulse periods less than one-half of the previously determined average pulse period, to again eliminate any contributions in the averaging process by noise and artifact signals, and provide a reliable final average pulse period. In this regard, FIG. 27 is a flow chart illustrating the average period determination by the digital processing subsystem of the present invention.

Figure 27:
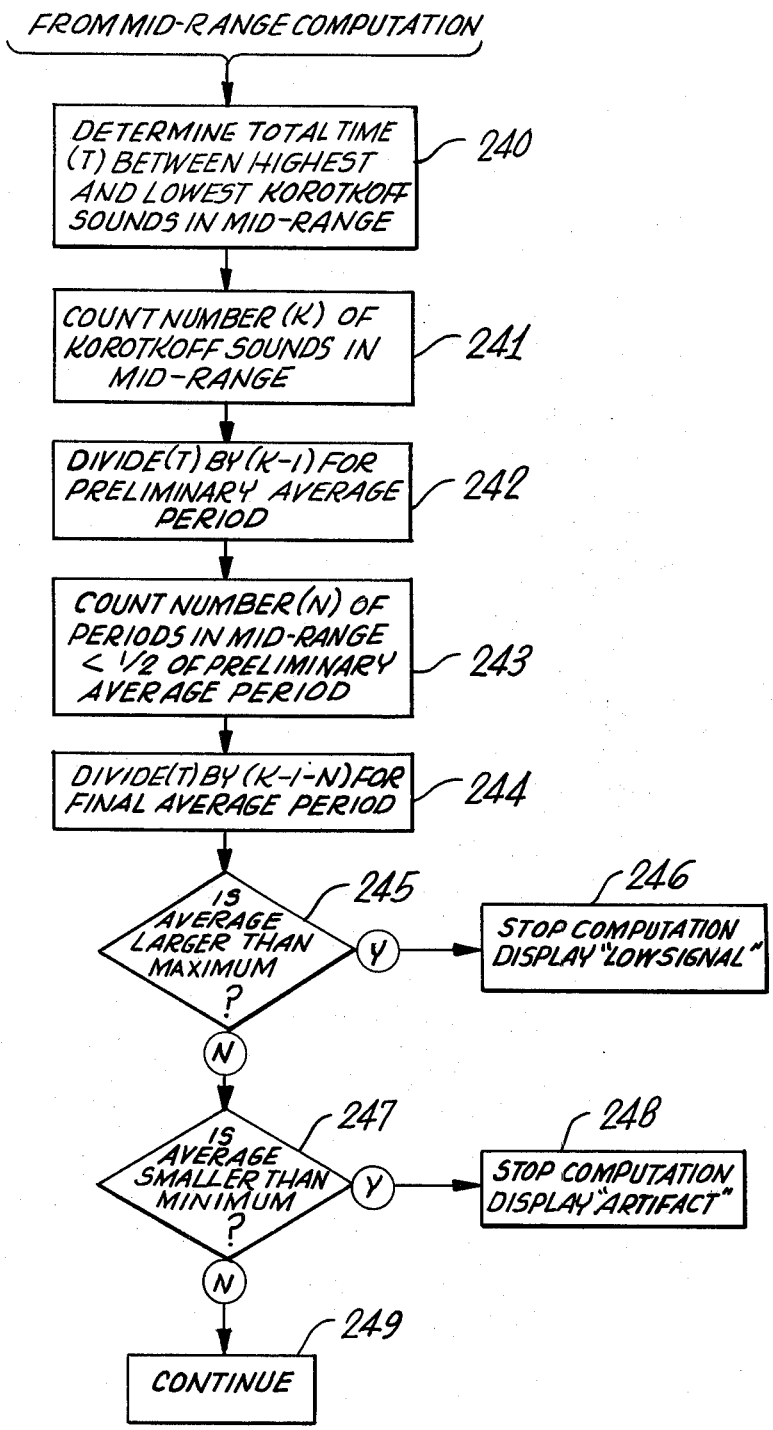

Step 240 in FIG. 27 calls for determination of the total time (T) between the highest and lowest korotkoff sound pulses occurring in the mid-range region. In step 241, the number (K) of the korotkoff sound pulses in the mid-range region is counted and, in step 242, the total time T is divided by one minus the number of korotkoff sounds in the mid-range (K−1) for a first preliminary average period determination.

In step 243, the number (N) of pulse period in the mid-range less than one-half of the preliminary average period is counted and, in step 244, a new final average period determination is made by dividing the total time T by one minus only the number of korotkoff sounds in the mid-range equal to or larger than one-half of the previously computed first average (K−1−N).

In steps 245 and 247, a determination is made after the final average period has been computed, whether or not the period falls within a predetermined acceptable range. If the final average period does not fall within that range, the measuring process is abandoned. In this regard, if the resultant average pulse period is too long, indicating a heart rate below a prescribed minimum rate, e.g., thirty pulses per minute, then computation is stopped in step 246 and a "low signal" indication is displayed to the operator.

If, on the other hand, an unusually short pulse period is found by test 247, indicating an excessively high heart rate, e.g., in excess of 200 pulses per minute, then the computation process is stopped at step 248 and an "artifact" indication is displayed to the operator which indicates that too many noise pulses or artifact pulses are appearing in the data and being accepted by the system as true korotkoff signals, thus giving the appearance of a misleading high heart rate determination and introducing a high degree of unreliability into the data, and calling for a repeat of the measurement process.

If the final average period determined in step 244 passes both of the tests 245, 247, indicating that the average period falls within the predetermined acceptable range, then the analysis process is continued via step 249.

Up to this point, all korotkoff sound signals had been stored in the shift register memory unchanged from the original storage provided at the output of the analog prescreening subsystem. Subsequently, the digital processing subsystem of the present invention modifies the stored data by normalizing all the korotkoff pulses to a standardized average and then performing various standardized spreading and smoothing techniques to ultimately provide a smooth, digitized waveform envelope for the korotkoff sound pulse stream, upon which systolic and diastolic blood pressure measurements can be reliably made.

The reason for normalizing all of the korotkoff pulses to a standardized average is that each measurement cycle will normally yield a different value of average korotkoff pulse amplitude and, therefore, subsequent testing and computation by the digital processing subsystem would have to be adjusted in each measurement cycle for the new average. In contrast, normalizing the data to the same prescribed average for all measurement cycles, while preserving the relative amplitudes of the korotkoff pulses throughout the entire korotkoff pulse spectrum, simplifies subsequent analysis by the digital processing system.

Figure 28:
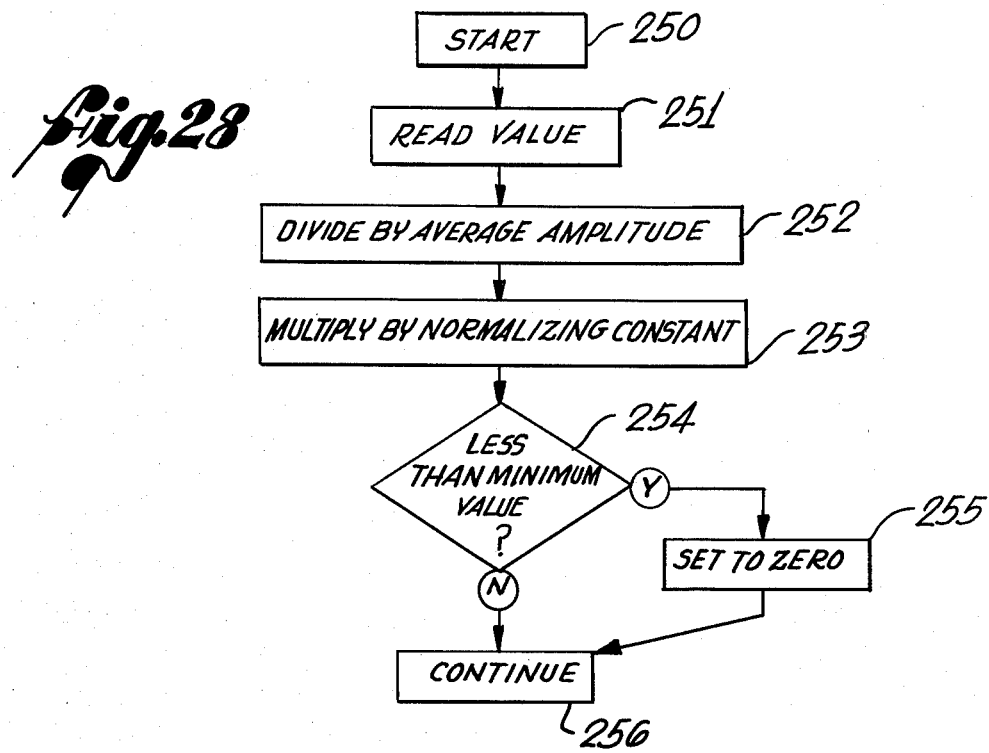

In this regard, FIG. 28 is a flow chart illustrating the normalization of korotkoff sound signal amplitudes as carried out by the digital processing subsystem. The process receives a start signal in step 250 and, in step 251, reads the value of the korotkoff pulse amplitude for the particular pulse being examined in the unsmoothed data represented by the original korotkoff pulse stream received from the prescreening subsystem. In step 252, the amplitude value read in step 251 is divided by the average korotkoff pulse amplitude previously determined for the mid-range region and, in step 253, the result of step 252 is multiplied by an appropriate normalizing constant to provide a new pulse amplitude relative to the standardized average.

At this point, further amplitude discrimination is performed upon the normalized data to further eliminate low level contributions due to noise and artifacts. This is accomplished at step 254 by testing each individual normalized korotkoff pulse amplitude against a prescribed minimum value. If the normalized pulse amplitude is too low, then the answer to question 254 is yes, the particular pulse amplitude value is set to zero in step 255 and the process is then continued at step 256 to the next pulse amplitude to be normalized. If the normalized pulse amplitude is above a prescribed minimum value, then the answer to question 254 is no, a new normalized value is stored, and the process is continued via step 256. The entire normalization process is applied to each and every korotkoff pulse amplitude in the entire korotkoff pulse spectrum and is not limited to simply the mid-range region, so that the result of the normalization process is a conversion of the entire pulse spectrum received from the prescreening subsystem to a standardized average for subsequent analysis by the digital processing subsystem.

Figure 30A:
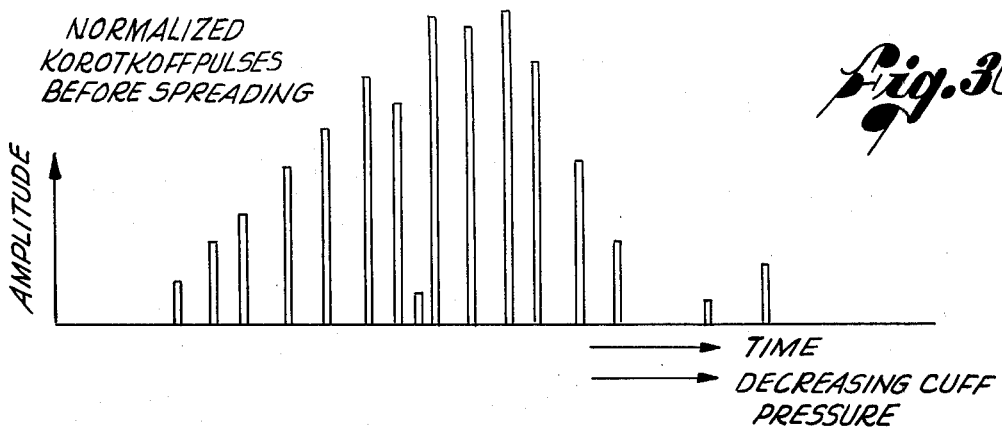

The resultant normalized korotkoff pulses produced by the normalization process described in connection with FIG. 28, are shown in FIG. 30a of the drawings.

Figure 30B:
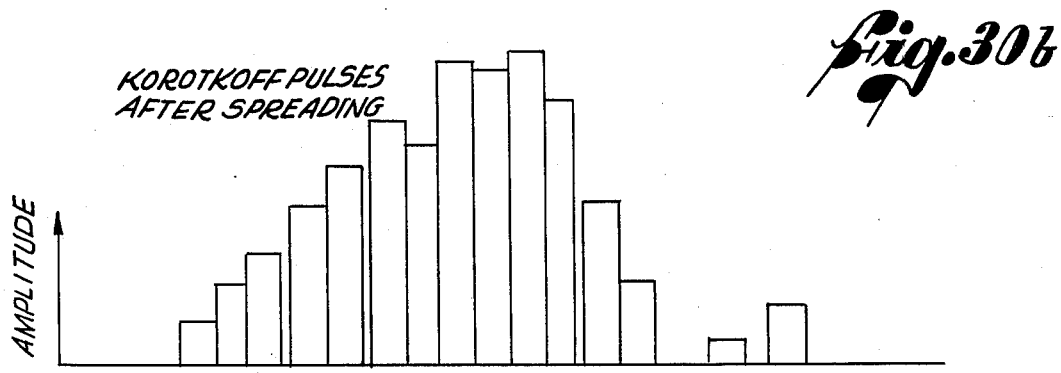
Figure 30C:
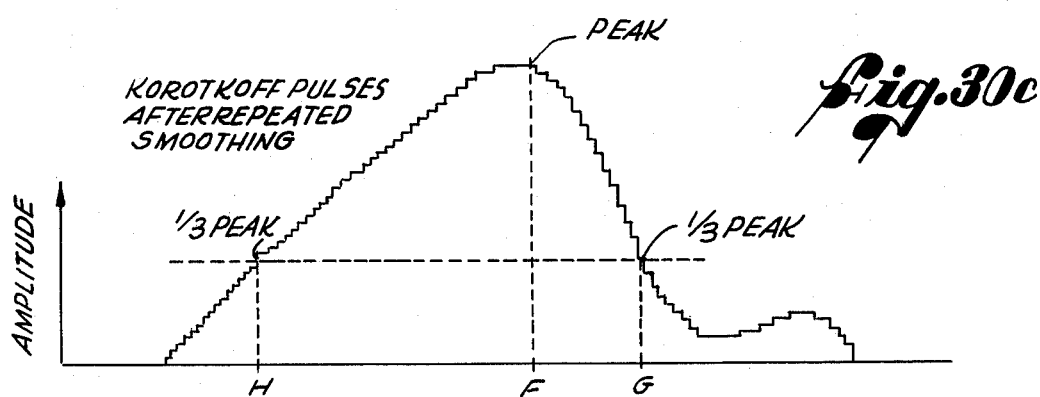

The digital processing subsystem next spreads and smooths the pulse stream data shown in FIG. 30a to obtain the spread pulse configuration shown in FIG. 30b and, after successive smoothing, produces the smoothed digitized waveform shown in FIG. 30c of the drawings. In this regard, while all of the data in the pulse stream is altered by the processes of normalization, spreading and smoothing, the locations of all of the original korotkoff sound signal pulses in the pulse stream from the prescreening subsystem (as indicated by FIG. 20) is preserved in memory so that the actual original korotkoff pulse locations can be applied as markers in the time and blood pressure domains upon the smoothed data curve of FIG. 30c. However, while all the locations of the original korotkoff pulses are preserved, their values are not, and the spreading and smoothing processes provide new values for every channel in the shift register to provide the smoothed curve shown in FIG. 30c.

Figure 29:
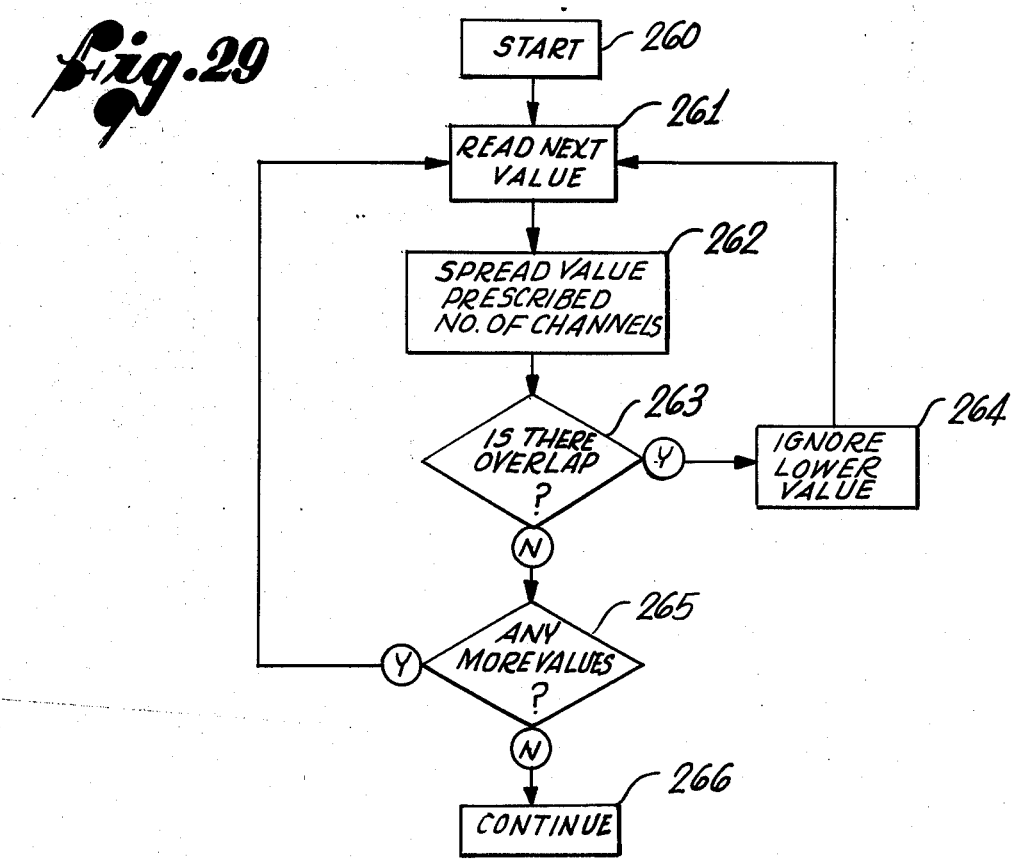

FIG. 29 is a flow chart illustrating the spreading of the normalized korotkoff pulse amplitude data of FIG. 30a to obtain the spread data spectrum shown in FIG. 30b. The spreading process starts in step 260 by accepting the previously normalized korotkoff pulse values. In step 261, the value of each korotkoff pulse amplitude is individually read. In step 262, the normalized amplitude value is spread over a width which is a prescribed number of memory channels. If overlap occurs with another pulse, the larger pulse amplitude value predominates. This is accomplished in test 263 which queries whether or not there has been overlap between two pulses during the spreading process of step 262. If the answer is yes, indicating overlap, then the lower value is ignored in step 264 and the process is continued again in step 261. If there is no overlap, then the answer to question 263 is no, and the process continues to step 265 which queries whether or not there are any more pulse values to be acted upon. If the answer is yes, then the process is continued by returning to step 261 and reading the next value. If the answer to question 265 is no, then the spreading process has been completed and the digital processing subsystem continues its determinations via step 266.

Figure 31:
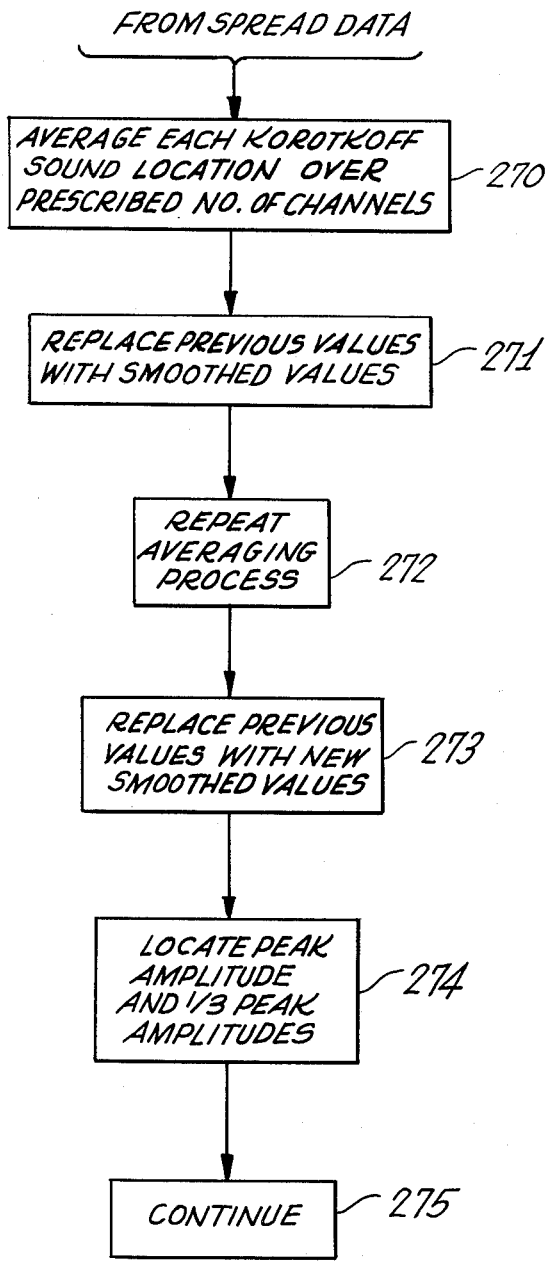

FIG. 31 is a flow chart illustrating the data smoothing process performed by the digital processing subsystem to convert the spread data of FIG. 30b to the smooth and digitized waveform shown in FIG. 30c. The smoothing process essentially averages the previously normalized and spread korotkoff pulse signals over a prescribed channel width, and these smoothed values replace the previously stored pulse amplitudes in the shift register. The same smoothing operation is performed twice in order to produce the waveform of FIG. 30c.

Referring now to FIG. 31, the smoothing process accepts the spread data resulting from the spreading process and, in step 270, averages each korotkoff sound pulse location over a prescribed number of memory channels. In step 271, the previously stored values in the shift register are replaced with the newly determined smoothed values.

After the first smoothing process has been completed, the averaging process is again repeated in step 272 upon the smoothed data and the previous smoothed values are replaced, in step 273, with new smoothed values to produce the digitized waveform of FIG. 30c. In step 274, the peak amplitude and one-third peak amplitudes are determined from the final smoothed waveform, and their locations are stored in memory. Point F corresponds to the peak location, and points G and H correspond to the one-third peak locations at the diastolic and systolic regions, respectively, in FIG. 30c. While one-third peak locations are chosen for subsequent analysis by the digital processing subsystem, the particular fractional peak amplitudes used could typically fall in the range of one-fifth to one-half without departing from the invention. Upon completion of the smoothing process, the digital processing subsystem continues its analysis via the step 275.

In accordance with the invention, a variety of tests are next performed at the extremities of the smoothed, digitized waveform of FIG. 30c, including location of minimum amplitude or slope reversal limits, pulse period tests, and systolic and diastolic slope projections, to determine three categories of diastolic pressure limits and two categories of systolic pressure limits which are subsequently used in the final determination of the most probable and reliable systolic and diastolic blood pressure levels of the patient.

Figure 32:
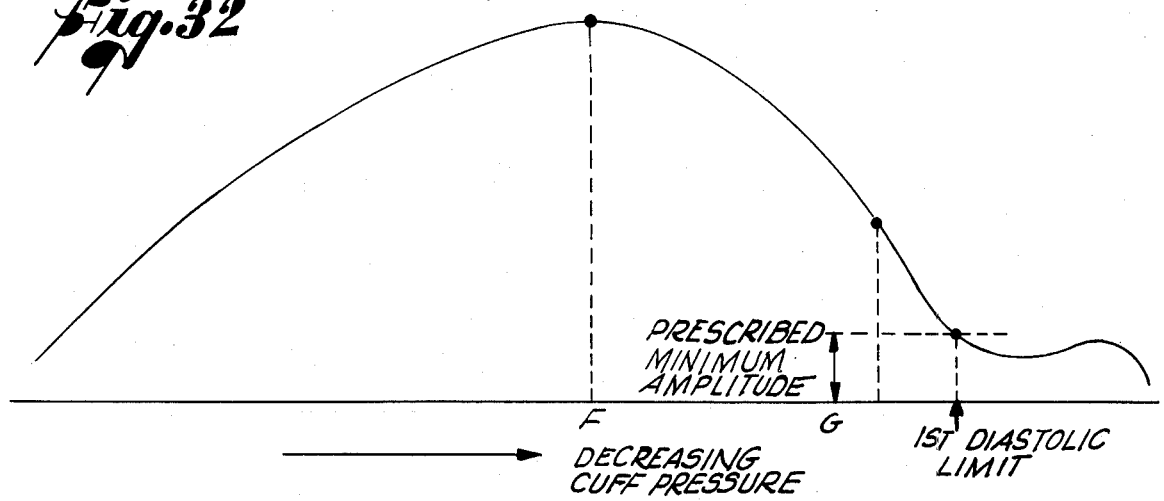

FIG. 32 again illustrates the smoothed waveform of FIG. 30c, upon which a simple test is performed to determine a first diastolic limit. In this test, the digital processing sub system examines every shift register location in sequence below the one-third peak amplitude G, going toward lower pressure. In this regard, if the amplitude drops to a prescribed minimum amplitude below the one-third peak amplitude, the pressure is read as the first diastolic limit.

Figure 33:
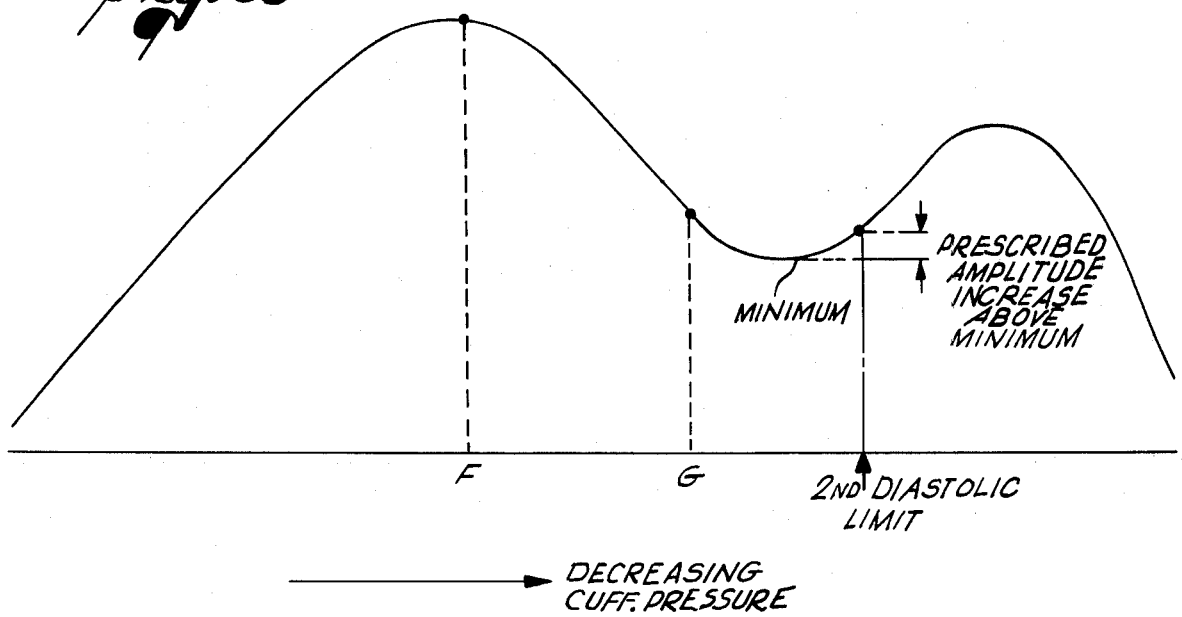

FIG. 33 is a graphical representation of the smoothed data illustrating the determination of a second diastolic limit. In performing the minimum amplitude test described in connection with FIG. 32, if the amplitude does not drop a prescribed minimum below the one-third peak amplitude at G, but reverses slope by passing through a minimum and then increasing in amplitude again, the second diastolic limit is determined at a maximum change of a prescribed number of amplitude units above the minimum amplitude encountered in passing through the slope reversal.

Figure 34:
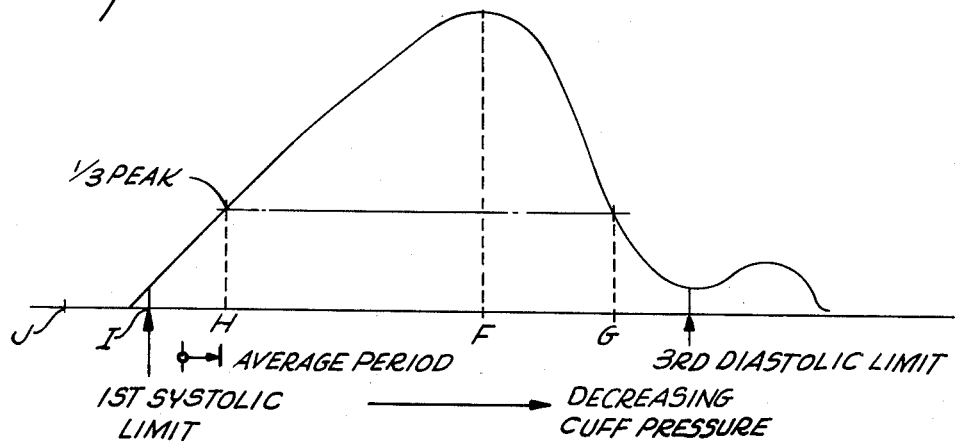

FIG. 34 is a graphical representation of the smoothed data and illustrates determination of a third diastolic limit and a first systolic limit by the digital processing subsystem. This is accomplished by performing a pulse period test at both ends of the pulse spectrum. For the systolic limit, all of the pulse periods (using the locations of the original korotkoff pulses) at higher pressures above the one-third peak amplitude location H of the smoothed waveform are examined, and the previously determined average pulse period (FIG. 27) is used as a criterion to find the highest systolic korotkoff pulse. The first pulse, moving toward the higher cuff pressures, which marks the boundary of a pulse period that is longer than one and one-half times the previously determined average pulse period is determined as the first systolic limit. In FIG. 34, the period between pulses I and J is more than one and one-half times the average pulse period and, therefore, the position of an original korotkoff pulse at location I is the first systolic limit.

The pulse period test is repeated at the diastolic end of the pulse spectrum. The same criterion is used as in the determination of the first systolic limit, except that determinations are made below the one-third peak at location G in going toward lower pressures. The first pulse period located that is again longer than one and one-half times the previously determined average pulse period, as determined by the original korotkoff pulse located at the higher blood pressure defining the beginning of that period, is stored in memory as the third diastolic limit.

Figure 35:
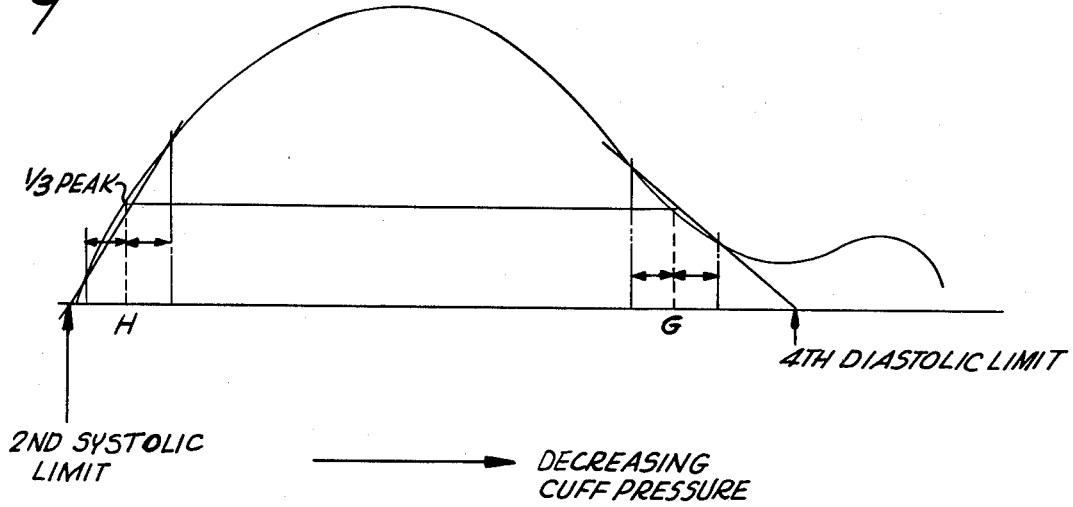

FIG. 35 is a graphical representation of the smoothed data illustrating the determination of a fourth diastolic limit and a second systolic limit by the digital processing subsystem. In this regard, the amplitudes of the smoothed korotkoff pulse distribution a prescribed channel width both above and below the upper one-third peak amplitude at location H and the lower one-third peak amplitude location G are determined and a straight line is drawn through each pair of points on opposite sides of the one-third peak amplitude locations. The intersections of those lines with the cuff pressure axis defines a second systolic limit and a fourth diastolic limit.

The systolic limit which is used for determination of systolic blood pressure is the location representing the lowest blood pressure determined by the two systolic limits. The diastolic limit used in the determination of diastolic blood pressure is the location corresponding to the highest blood pressure indicated by any of the four diastolic limits.

Starting at the aforementioned finally determined systolic limit, the first korotkoff pulse location below that limit, i.e., lower in pressure, defines the systolic blood pressure. In order to average the digital resolution uncertainty, the actual systolic pressure computed and displayed by the digital processing system is the equivalent of a blood pressure which is one-half of the predetermined average pulse period (FIG. 27) higher in magnitude than would otherwise be indicated by the actual korotkoff sound signal pulse location. The top three korotkoff pulse locations are then examined, i.e., the highest systolic pulse and the two korotkoff pulses immediate below the first pulse, and the pair of pulse periods between those three korotkoff pulses are added. The sum of those pulse periods must be larger than one and one-half times the previously determined average pulse period or the measurement is considered unreliable and is abandoned, with an "artifact" indication being displayed to the operator.

Similarly, starting at the previously determined final diastolic limit, the first original korotkoff pulse location above that diastolic limit (higher in pressure) is used to determine the diastolic pressure. Again, in order to average the digital resolution uncertainty, the actual pressure displayed to the operator is the equivalent of one-half of the predetermined average pulse period lower in pressure than that otherwise indicated by the diastolic limit korotkoff pulse.

The three lowest korotkoff sound signal pulse locations, i.e., the diastolic limit korotkoff pulse and the two pulses above that pulse in pressure, are then examined for possible noise or artifacts. As in the computation of the systolic blood pressure, the sum of the two pulse periods must be larger than one and one-half times the predetermined average pulse period, or the measurement is terminated and an "artifact" indication is displayed to the operator calling for a repetition of the measurement cycle.

Heart rate is determined by the digital processing system by taking the reciprocal of the average pulse period for the mid-range region determined in the process described in connection with FIG. 27.

It will be apparent from the foregoing description that those of ordinary skill in the data processing art should be able to use a wide variety of computer implementations in both hardware and software to practice many of the analysis and evaluation techniques embodied within the methods and apparatus of the present invention. By way of example, the invention may be practiced on a Model No. 4004 Central Processor Unit manufactured by INTEL Corp., 3065 Bowers Ave., Santa Clara, Calif., supplemented by one RAM unit, Model No. 4002, and 12 ROM units, Model No. 4308.

The new and improved electronic sphygmomanometer system of the present invention is extremely accurate, reliable and easy to use. The system provides enhanced precision in separating true korotkoff sound signals from artifact and noise signals and is quick to inform medical personnel of any conditions which indicate the presence of unreliable data. Hence, the system of the present invention minimizes the time consuming and error-prone aspects of manual techniques for the measurement of human blood pressure and heart rate and obviates the need for a high degree of skill and subjective expertise on the part of medical personnel required to make such measurements.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. In an electronic sphygmomanometer, the combination comprising:
   means for providing detected korotkoff sounds and associated korotkoff sound precursors as electrical signals, each of said korotkoff sound precursors being included in the waveforms relating solely to the individual korotkoff sound signal with which that precursor is associated; and
   means for analyzing the waveforms of all said electrical signals to determine selectively the presence of specified korotkoff sound precursors and the conformity of such precursors with predetermined waveform characteristics, whereby those electrical signals having waveforms representative of true korotkoff sounds are separated from those electrical signals which do not represent true korotkoff sounds.

2. A combination as set forth in claim 1, wherein said means for analyzing said waveforms includes a diastolic channel, a systolic channel and an amplitude channel, the electrical output from said amplitude channel being selectively gated by either of said diastolic channel and said systolic channel.

3. A combination as set forth in claim 2, wherein said diastolic channel evaluates the amplitude of a waveform precursor to a korotkoff spike.

4. A combination as set forth in claim 2, wherein said diastolic channel evaluates the area of a waveform precursor to a korotkoff spike.

5. A combination as set forth in claim 2, wherein said diastolic channel evaluates the time duration of a waveform precursor to a korotkoff spike.

6. A combination as set forth in claim 2, wherein said diastolic channel evaluates the amplitude, area and time duration of a waveform precursor to a korotkoff spike.

7. A combination as set forth in claim 2, wherein said systolic channel evaluates the slope of the leading edge of a korotkoff spike.

8. A combination as set forth in claim 2, wherein said systolic channel evaluates the duration of the leading edge of a korotkoff spike.

9. A combination as set forth in claim 2, wherein said systolic channel evaluates the slope and time duration of the leading edge of a korotkoff spike.

10. The combination as set forth in claim 2, wherein said amplitude channel measures the amplitude of a korotkoff spike.

11. The combination as set forth in claim 10, wherein said amplitude channel measures said amplitude along the trailing edge of said korotkoff spike.

12. A combination as set forth in claim 1, wherein said means for analyzing said waveforms includes:
   means for measuring the amplitude, area and time duration of a waveform precursor to a korotkoff spike; and
   means for measuring the slope and time duration of the leading edge of a korotkoff spike.

13. In an electronic sphygmomanometer for analyzing korotkoff sounds produced by an auscultation blood pressure measuring process, the combination comprising:
   first means for providing korotkoff sounds and associated korotkoff sound precursors as input electrical signals, each of said korotkoff sound precursors being included in the waveforms relating solely to the individual korotkoff sound signal with which that precursor is associated;
   second means for analyzing the waveforms of all of said input electrical signals to determine selectively the presence of specified korotkoff sound precursors and their conformity with predetermined waveform characteristics; and
   third means responsive to said second means for selectively producing output electrical signals in time correlation only with those input electrical signals corresponding to true korotkoff sounds, whereby those input electrical signals representing true korotkoff sounds are separated from artifact and noise signals.

14. A combination as set forth in claim 13, wherein said third means produces output electrical signals proportional in amplitude to those input electrical signals representing true korotkoff sounds.

15. A combination as set forth in claim 13, wherein said second means analyzes the amplitude of portions of said waveform.

16. A combination as set forth in claim 13, wherein said second means analyzes the area of portions of said waveform.

17. A combination as set forth in claim 13, wherein said second means analyzes the time duration of portions of said waveform.

18. An electronic sphygmomanometer as set forth in claim 17, and further including:
   first means for rectifying the waveforms of each of said input electrical signals;
   second means for integrating the area under the rectified waveform produced by said first means.

19. Apparatus as set forth in claim 18, wherein said means for integrating the area requires that a minimum amplitude threshold be exceeded to begin integration.

20. Apparatus as set forth in claim 18, wherein said means for integrating the area requires a minimum time period for the electrical output of the integration to exceed a predetermined level.

21. Apparatus as set forth in claim 18, and further including:
   discrimination means for measuring the magnitude of the electrical output from said second means.

22. A combination as set forth in claim 13, wherein said second means analyzes the slope of portions of said waveform.

23. An electronic sphygmomanometer, comprising:
   input means for providing korotkoff sounds and associated korotkoff sound precursors as input electrical signals, each of said korotkoff sound precursors being included in the waveforms relating solely to the individual korotkoff sound signal with which that precursor is associated;
   waveform analysis means for receiving and analyzing the waveforms of all of said input electrical signals to determine selectively the presence of specified korotkoff sound precursors and the conformity of each individual input electrical signal with predetermined waveform characteristics and to produce an electrical output indicative of the presence or absence of such conformity, and thereby the presence or absence of said specified precursors, for each such input electrical signal; and
   output means responsive to said electrical output from said waveform analysis means for producing output electrical signals indicative of only those input electrical signals having waveforms representative of the occurrence of true korotkoff sounds.

24. A sphygmomanometer as set forth in claim 23, wherein said waveform analysis means measures the conformity of input electrical signals with characteristics of a first class of generalized waveforms.

25. An electronic sphygmomanometer as set forth in claim 24, wherein said waveform analysis means also measures the conformity of said input electrical signals with the characteristics of a second class of generalized waveforms.

26. An electronic sphygmomanometer as set forth in claim 23, wherein said waveform analysis means measures the conformity of said input electrical signals with characteristics of a plurality of classes of generalized waveforms.

27. An electronic sphygmomanometer as set forth in claim 23, wherein said waveform analysis means includes means for evaluating the amplitude, area and time duration of a waveform precursor occurring immediately prior to a korotkoff spike and of opposite polarity from said spike.

28. An electronic sphygmomanometer as set forth in claim 23, wherein said waveform analysis means includes means for evaluating the time duration and minimum slope of the leading edge of a korotkoff spike.

29. An electronic sphygmomanometer as set forth in claim 28, and further including:
   rectifier means for rectifying the waveforms of all of said input electrical signals;
   means for differentiating the electrical output of said rectifier means;
   discriminator means for measuring the amplitude of electrical outputs from said differentiator means; and
   timing means for measuring the duration of electrical output from said discriminator means.

30. An electronic sphygmomanometer as set forth in claim 23, wherein said output means measures the amplitude of each korotkoff spike occurring in an input electrical waveform and produces an output electrical signal having an amplitude proportional to the base to peak amplitude of said spike.

31. An electronic sphygmomanometer as set forth in claim 30, wherein said amplitude is measured along the trailing edge of said korotkoff spike.

32. An electronic sphygmomanometer as set forth in claim 30, and further including:
   first rectifier means for rectifying the waveforms of all of said input electrical signals;
   differentiator means for differentiating the electrical output of said first rectifier means;
   second rectifier means for rectifying the electrical output of said differentiator means; and
   integration means for integrating the electrical output of said rectifier means.

33. Apparatus as set forth in claim 32, wherein said second rectifier means isolates the trailing edge of each korotkoff spike.

34. Apparatus as set forth in claim 32, wherein said integration means produces output electrical pulses proportional in amplitude to the base to peak amplitude of each korotkoff spike.

35. Apparatus as set forth in claim 34, wherein said amplitude is measured along the trailing edge of each korotkoff spike.

36. An electronic sphgmomanometer as set forth in claim 32 and further including:
   gating means under the control of said waveform analysis means for selectively passing electrical output as pulses from said second rectifier means to said integration means.

37. Apparatus as set forth in claim 36, wherein said gating means enables passage of electrical output from said rectifier means to said integration means only when said waveform analysis means produces an electrical output indicative of the presence of conformity between said input electrical signals and said predetermined waveform characteristics.

38. Apparatus as set forth in claim 36, and further including:

control means for controlling the output of said gating means in response to a variable amplitude threshold applied to said pulses.

39. Apparatus as set forth in claim 38, wherein said variable threshold prevents passage of relatively small pulses for a period of time after passage of relatively larger pulses.

40. Apparatus as set forth in claim 38, wherein said control means includes a peak rectifier electrical circuit.

41. Apparatus as set forth in claim 40, wherein said control means includes a discriminator latch and said gating means is enabled and disabled in accordance with the electrical output state of said latch.

42. Apparatus as set forth in claim 41, wherein said peak rectifier receives an electrical input from said output means.

43. Apparatus as set forth in claim 38, wherein said control means includes a discriminator latch circuit.

44. Apparatus as set forth in claim 38, wherein said control means includes both a peak rectifier and discriminator latch.

45. An electronic sphygmomanometer as set forth in claim 23, wherein said waveform analysis means includes a first channel for evaluating the amplitude, area and time duration of a waveform precursor to a korotkoff spike and a second channel for evaluating the slope and time duration of the leading edge of a korotkoff spike.

46. An electrical sphygmomanometer, comprising:
first means for providing electrical waveforms representing korotkoff sounds and associated korotkoff sound precursors, each of said korotkoff sound precursors being included in the waveforms relating solely to the individual korotkoff sound signal with which that precursor is associated;
second means for analyzing the amplitude selectively of portions of said waveforms and producing an output pulse stream representative of the amplitude and occurrence of those of said waveforms representing true korotkoff events;
third means for determining selectively the presence of specified korotkoff sound precursors by the correlation of said electrical waveforms with prescribed waveform conditions;
fourth means for controlling the output of said first means in response to waveform analysis by said second means; and
fifth means for analyzing the electrical output of said first means to determine blood pressure.

47. An electronic sphygmomanometer as set forth in claim 46, wherein said fifth means also determines heart rate.

48. Apparatus as set forth in claim 46, wherein said first means, said second means, said third means and said fourth means are analog electrical systems.

49. Apparatus as set forth in claim 46, wherein said fifth means is a digital system.

50. Apparatus as set forth in claim 46, wherein said first means, said second means, said third means, and said fourth means are analog systems and said fifth means is a digital system.

51. In an electronic sphygmomanometer for analyzing korotkoff sounds produced by an auscultation blood pressure measuring process, the combination comprising:
first means for providing korotkoff sounds and associated korotkoff sound precursors as input electrical signals, each of said korotkoff sound precursors being included in the waveforms relating solely to the individual korotkoff sound signal with which that precursor is associated;
second means for prescreening selectively for the presence of specified korotkoff sound precursors the waveforms of all of said input electrical signals from said first means and producing output electrical signals in time correlation only with those input electrical signals corresponding to the occurrence of true korotkoff events; and
third means for analyzing the output electrical signals from said second means to determine blood pressure.

52. Apparatus as set forth in claim 51, wherein said third means further screens said output electrical signals to eliminate those electrical signals representing events other than the occurrence of true korotkoff events.

53. Apparatus as set forth in claim 51, wherein said second means is an analog system.

54. Apparatus as set forth in claim 51, wherein said third means is a digital system.

55. Apparatus as set forth in claim 54, wherein said second means includes a diastolic channel, a systolic channel and an amplitude channel.

56. Apparatus as set forth in claim 55, wherein said diastolic channel evaluates the amplitude, area and time duration of a waveform precursor to a korotkoff spike.

57. Apparatus as set forth in claim 55, wherein said systolic channel evaluates the slope and time duration of the leading edge of a korotkoff spike.

58. Apparatus as set forth in claim 55, wherein said amplitude channel measures the amplitude of a korotkoff spike.

59. Apparatus as set forth in claim 58, wherein said amplitude channel measures said amplitude along the trailing edge of said korotkoff spike.

60. Apparatus as set forth in claim 51, wherein said third means also determines heart rate.

61. Apparatus as set forth in claim 51, wherein said second means is an analog system and said third means is a digital system.

62. An electronic sphygmomanometer, comprising:
first means for detecting electrical waveforms representing korotkoff sounds and producing output pulses representing said korotkoff sounds;
second means for controlling the output of said first means in response to a variable amplitude threshold applied to said pulses.

63. Apparatus as set forth in claim 62, wherein said variable threshold prevents passage of relatively small pulses for a period of time after passage of relatively larger pulses.

64. Apparatus as set forth in claim 63, wherein said peak rectifier receives an electrical input from said first means.

65. Apparatus as set forth in claim 62, wherein said second means includes a peak rectifier electrical circuit.

66. Apparatus as set forth in claim 62, wherein said second means includes a discriminator latch circuit.

67. Apparatus as set forth in claim 62, wherein said first means includes a control gate.

68. Apparatus as set forth in claim 67, wherein said second means includes a discriminator latch and said control gate is enabled and disabled in accordance with the electrical output state of said latch.

69. Apparatus as set forth in claim 63, wherein said second means includes both a peak rectifier and discriminator latch.

70. Apparatus as set forth in claim 62, wherein said first means includes a control gate, said second means includes a peak rectifier and discriminator latch, and said control gate is opened and closed to respectively pass and block the output pulses from said first means in accordance with the electrical output state of said latch.

71. An electronic sphygmomanometer, comprising:
first means for providing electrical waveforms representing korotkoff sounds and associated korotkoff sound precursors, each of said korotkoff sound precursors being included in the waveforms relating solely to the individual korotkoff sound signal with which that precursor is associated;
second means for analyzing the amplitude selectively of portions of said waveforms and producing an output pulse stream representing the amplitudes and occurrences of those of said waveforms representing true korotkoff events;
and third means for determining selectively the presence of specified korotkoff sound precursors by the correlation of said electrical waveforms with prescribed waveform characteristics and for controlling the output of said second means in response to the waveform analysis of said third means.

72. Apparatus as set forth in claim 71, and further including:
fourth means for frequency shaping the electrical input to said second means.

73. Apparatus as set forth in claim 71, and further including:
fifth means for frequency shaping the electrical input to said third means.

74. Apparatus as set forth in claim 73, wherein said fifth means provides a pass band substantially in the range from $\frac{1}{2}$ Hz. to 20 Hz.

75. Apparatus as set forth in claim 72, wherein said fourth means provides a first pass band substantially in the range from 15 Hz. to 150 Hz. and a second pass band substantially in the range from $\frac{1}{2}$ Hz. to 10 Hz., said second pass band being attenuated relative to said first pass band.

76. In an electronic sphygmomanometer, the combination comprising:
first means for determining the amplitude selectively of the trailing edge of a korotkoff signal spike and producing an output pulse proportional thereto;
second means for correlating and measuring the amplitude, area and time duration selectively of a precursor bulge preceding a korotkoff spike;
third means for correlating and measuring the slope and time duration selectively of a leading edge of a korotkoff spike; and
fourth means responsive to an indication of successful correlation from either of said second means and said third means for selectively enabling said first means.

77. A combination as set forth in claim 76, wherein said second means is a diastolic waveform analysis means.

78. A combination as set forth in claim 76, wherein said third means is a systolic waveform analysis means.

79. A combination as set forth in claim 76, wherein said first means includes a control gate for selectively passing or blocking the output pulses from said first means.

80. A combination as set forth in claim 76, and further including;
fifth means for selecting enabling said first means in response to a variable amplitude threshold applied to each output pulse from said first means.

81. Apparatus as set forth in claim 80, wherein said variable amplitude threshold prevents passage of relatively small output pulses from said first means for a period of time after the passage of a relatively larger output pulse from said first means.

82. A combination as set forth in claim 76, wherein said first means provides electrical input to an integrator within said first means.

83. Apparatus as set forth in claim 82, and further including:
fifth means for selectively enabling said first means and simultaneously controlling charging and discharging of said integrator.

84. Apparatus as set forth in claim 83 wherein said fifth means includes a discriminator latch.

85. Apparatus as set forth in claim 83, wherein said fifth means includes a peak rectifier and discriminator latch circuit and said peak rectifier receives an electrical input from said first means.

86. Apparatus as set forth in claim 82, and further including:
fifth means for controlling the electrical output of said first means in response to a variable amplitude threshold applied to electrical output pulses from said first means and also controlling, charging and discharging of said integrator.

87. A combination as set forth in claim 76, wherein the electrical input to said first means is frequency shaped to provide a first pass band substantially in the range of 15 Hz. to 150 Hz. and a second pass band substantially in the range of $\frac{1}{2}$ Hz. to 10 Hz., said second pass band being attenuated relative to said first pass band.

88. A combination as set forth in claim 76, wherein the electrical input to said second means and said third means is frequency shaped to provide a pass band substantially in the range of $\frac{1}{2}$ Hz. to 20 Hz.

89. In a method of blood pressure measurement, the steps of:
providing electrical input waveform signals representing korotkoff sounds and associated korotkoff sound precursors, each of said korotkoff sound precursors being included in the waveforms relating solely to the individual korotkoff sound signal with which that precursor is associated; and
analyzing the waveforms of all of said signals to determine selectively the presence of specified korotkoff sound precursors and the conformity of such precursors with predetermined waveform characteristics, whereby those waveforms representative of true korotkoff sounds are separated from those waveforms which do not represent true korotkoff sounds.

90. A method as set forth in claim 89, wherein said analyzing step includes:
measuring the amplitude of a waveform precursor to a korotkoff spike.

91. A method as set forth in claim 89, wherein said analyzing step includes:
measuring the area of a waveform precursor to a korotkoff spike.

92. A method as set forth in claim 89, wherein said analyzing step includes:
measuring the time duration of a waveform precursor to a korotkoff spike.

93. A method as set forth in claim 89, wherein said analyzing step includes:
   measuring the slope of the leading edge of a korotkoff spike.

94. A method as set forth in claim 89, wherein said analyzing step includes:
   measuring the time duration of the leading edge a korotkoff spike.

95. A method as set forth in claim 89, wherein said analyzing step includes:
   measuring the amplitude of a korotkoff spike.

96. A method as set forth in claim 89, wherein said analyzing step includes:
   measuring the amplitude of a korotkoff spike along the trailing edge of the korotkoff spike.

97. In an electronic sphygmomanometer, the combination comprising:
   first means for determimimg the amplitude selectively of the trailing edge of a korotkoff signal spike and producing an output pulse proportional thereto;
   second means for correlating and measuring the amplitude, area and time duration selectively of a precursor bulge preceding a korotkoff spike;
   third means responsive to an indication of successful correlation from said second means for selectively enabling said first means.

98. In an electronic sphygmomanometer, the combination comprising:
   first means for determining the amplitude selectively of the trailing edge of a korotkoff signal spike and producing an output pulse proportional thereto;
   second means for correlating and measuring the slope and time duration selectively of a leading edge of a korotkoff spike; and
   third means responsive to an indication of successful correlation from said second means for selectively enabling said first means.

99. In an electronic sphygmomanometer, the combination comprising:
   first means for correlating and measuring the amplitude, area and time duration selectively of a precursor bulge preceding a korotkoff spike; and
   second means for correlating and measuring the slope and time duration selectively of a leading edge of a korotkoff spike.

* * * * * rotkoff sounds are separated from artifact and noise signals.

14. A combination as set forth in claim 13, wherein said third means produces output electrical signals proportional in amplitude to those input electrical signals representing true korotkoff sounds.

15. A combination as set forth in claim 13, wherein said second means analyzes the amplitude of portions of said waveform.

16. A combination as set forth in claim 13, wherein said second means analyzes the area of portions of said waveform.

17. A combination as set forth in claim 13, wherein said second means analyzes the time duration of portions of said waveform.

18. An electronic sphygmomanometer as set forth in claim 17, and further including:
   first means for rectifying the waveforms of each of said input electrical signals;
   second means for integrating the area under the rectified waveform produced by said first means.

19. Apparatus as set forth in claim 18, wherein said means for integrating the area requires that a minimum amplitude threshold be exceeded to begin integration.

20. Apparatus as set forth in claim 18, wherein said means for integrating the area requires a minimum time period for the electrical output of the integration to exceed a predetermined level.

21. Apparatus as set forth in claim 18, and further including:
   discrimination means for measuring the magnitude of the electrical output from said second means.

22. A combination as set forth in claim 13, wherein said second means analyzes the slope of portions of said waveform.

23. An electronic sphygmomanometer, comprising:
   input means for providing korotkoff sounds and associated korotkoff sound precursors as input electrical signals, each of said korotkoff sound precursors being included in the waveforms relating solely to the individual korotkoff sound signal with which that precursor is associated;
   waveform analysis means for receiving and analyzing the waveforms of all of said input electrical signals to determine selectively the presence of specified korotkoff sound precursors and the conformity of each individual input electrical signal with predetermined waveform characteristics and to produce an electrical output indicative of the presence or absence of such conformity, and thereby the presence or absence of said specified precursors, for each such input electrical signal; and
   output means responsive to said electrical output from said waveform analysis means for producing output electrical signals indicative of only those input electrical signals having waveforms representative of the occurrence of true korotkoff sounds.

24. A sphygmomanometer as set forth in claim 23, wherein said waveform analysis means measures the conformity of input electrical signals with characteristics of a first class of generalized waveforms.

25. An electronic sphygmomanometer as set forth in claim 24, wherein said waveform analysis means also measures the conformity of said input electrical signals with the characteristics of a second class of generalized waveforms.

26. An electronic sphygmomanometer as set forth in claim 23, wherein said waveform analysis means measures the conformity of said input electrical signals with characteristics of a plurality of classes of generalized waveforms.

27. An electronic sphygmomanometer as set forth in claim 23, wherein said waveform analysis means includes means for evaluating the amplitude, area and time duration of a waveform precursor occurring immediately prior to a korotkoff spike and of opposite polarity from said spike.

28. An electronic sphygmomanometer as set forth in claim 23, wherein said waveform analysis means includes means for evaluating the time duration and minimum slope of the leading edge of a korotkoff spike.

29. An electronic sphygmomanometer as set forth in claim 28, and further including:
   rectifier means for rectifying the waveforms of all of said input electrical signals;
   means for differentiating the electrical output of said rectifier means;
   discriminator means for measuring the amplitude of electrical outputs from said differentiator means; and
   timing means for measuring the duration of electrical output from said discriminator means.

30. An electronic sphygmomanometer as set forth in claim 23, wherein said output means measures the amplitude of each korotkoff spike occurring in an input electrical waveform and produces an output electrical signal having an amplitude proportional to the base to peak amplitude of said spike.

31. An electronic sphygmomanometer as set forth in claim 30, wherein said amplitude is measured along the trailing edge of said korotkoff spike.

32. An electronic sphygmomanometer as set forth in claim 30, and further including:
   first rectifier means for rectifying the waveforms of all of said input electrical signals;
   differentiator means for differentiating the electrical output of said first rectifier means;
   second rectifier means for rectifying the electrical output of said differentiator means; and
   integration means for integrating the electrical output of said rectifier means.

33. Apparatus as set forth in claim 32, wherein said second rectifier means isolates the trailing edge of each korotkoff spike.

34. Apparatus as set forth in claim 32, wherein said integration means produces output electrical pulses proportional in amplitude to the base to peak amplitude of each korotkoff spike.

35. Apparatus as set forth in claim 34, wherein said amplitude is measured along the trailing edge of each korotkoff spike.

36. An electronic sphgmomanometer as set forth in claim 32 and further including:
   gating means under the control of said waveform analysis means for selectively passing electrical output as pulses from said second rectifier means to said integration means.

37. Apparatus as set forth in claim 36, wherein said gating means enables passage of electrical output from said rectifier means to said integration means only when said waveform analysis means produces an electrical output indicative of the presence of conformity between said input electrical signals and said predetermined waveform characteristics.

38. Apparatus as set forth in claim 36, and further including:

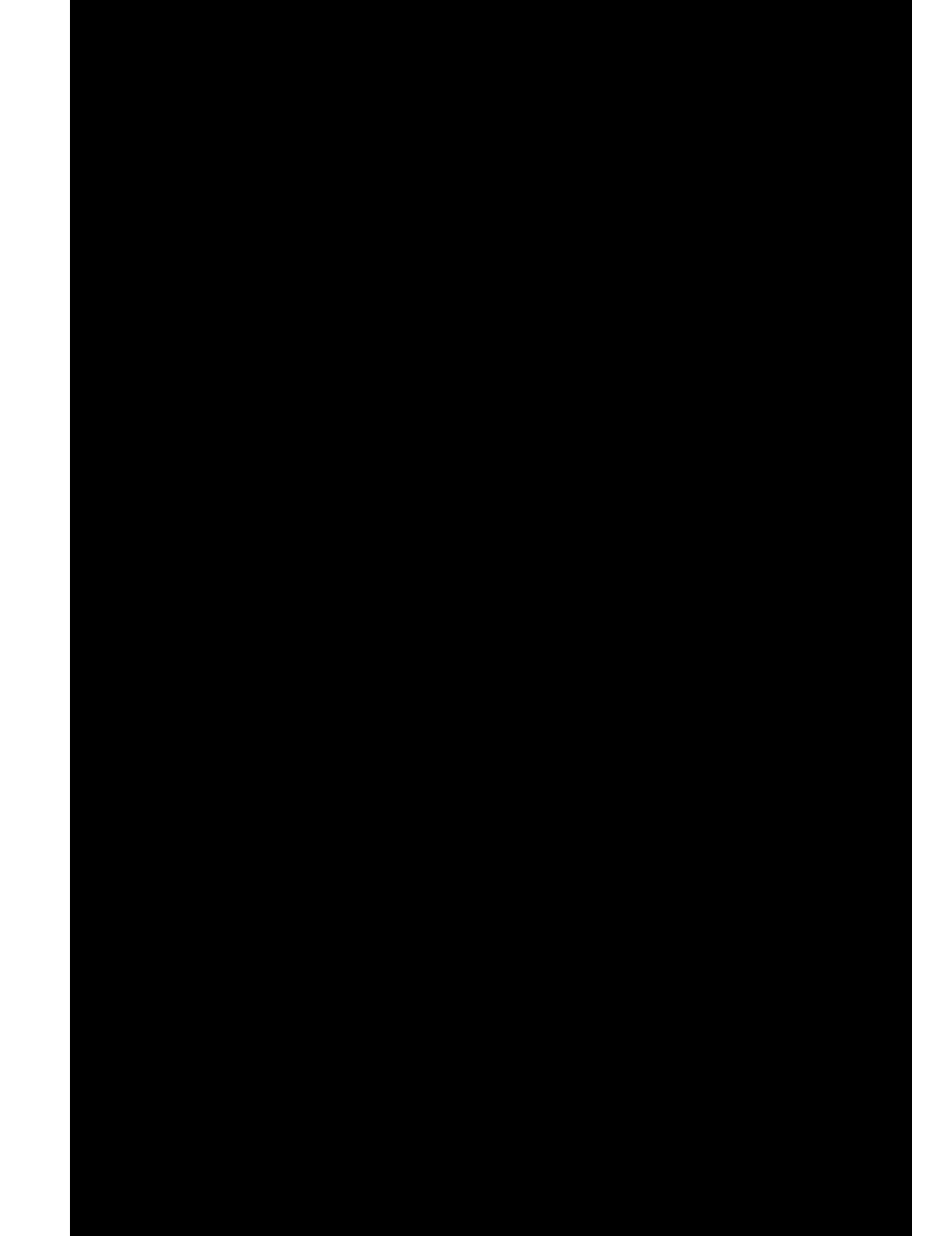

UNITED STATES PATENT AND TRADEMARK OFFICE
CERTIFICATE OF CORRECTION

PATENT NO. : 4,313,445
DATED : February 2, 1982
INVENTOR(S) : Heinz W. Georgi

It is certified that error appears in the above-identified patent and that said Letters Patent is hereby corrected as shown below:

Column 12, line 39, delete "ausculation" and insert therefor -- auscultation --.

Column 15, line 26, delete "occurence" and insert therefor -- occurrence --.

Column 16, line 6, delete "fuction" and insert therefor -- function --.

Column 16, line 50, delete "is" and insert therefor -- are --.

Column 20, line 53, delete "9b" and insert therefor -- 19b --.

Column 20, line 67, delete "FIGS." and insert therefor -- FIG. --.

Column 30, line 66, delete "immediate" and insert therefore -- immediately --.

Signed and Sealed this

Twenty-seventh Day of December 1983

[SEAL]

Attest:

GERALD J. MOSSINGHOFF

Attesting Officer

Commissioner of Patents and Trademarks